(12) United States Patent
Cawood et al.

(10) Patent No.: US 11,697,824 B2
(45) Date of Patent: Jul. 11, 2023

(54) VECTOR FOR THE PRODUCTION OF AAV PARTICLES

(71) Applicant: OXFORD GENETICS LIMITED, Oxford (GB)

(72) Inventors: Ryan Cawood, Oxford (GB); Alissa Sarah Bray, Oxford (GB); Thomas Augustus Payne, Oxford (GB)

(73) Assignee: Oxford Genetics Limited, Oxfordshire (GB)

( * ) Notice: Subject to any disclaimer, the term of this patent is extended or adjusted under 35 U.S.C. 154(b) by 281 days.

(21) Appl. No.: 16/768,844

(22) PCT Filed: Jan. 18, 2019

(86) PCT No.: PCT/GB2019/050134
§ 371 (c)(1),
(2) Date: Jun. 1, 2020

(87) PCT Pub. No.: WO2019/141993
PCT Pub. Date: Jul. 25, 2019

(65) Prior Publication Data
US 2021/0163987 A1    Jun. 3, 2021

(30) Foreign Application Priority Data
Jan. 19, 2018 (GB) .................................... 1800903

(51) Int. Cl.
*C12N 15/86* (2006.01)
*C12N 15/864* (2006.01)
*C12N 15/861* (2006.01)

(52) U.S. Cl.
CPC .... *C12N 15/86* (2013.01); *C12N 2750/14143* (2013.01); *C12N 2750/14152* (2013.01); *C12N 2840/203* (2013.01)

(58) Field of Classification Search
CPC ............. C12N 2840/203; C12N 15/86; C12N 2750/14152; C12N 2750/14143; C12N 15/864; C12N 15/8645
See application file for complete search history.

(56) References Cited

U.S. PATENT DOCUMENTS

| | | | |
|---|---|---|---|
| 5,622,856 A | 4/1997 | Natsoulis | |
| 7,115,391 B1 | 10/2006 | Chen et al. | |
| 10,533,188 B2 | 1/2020 | Hermens et al. | |
| 10,858,631 B2 * | 12/2020 | Vink | C07K 14/005 |
| 2002/0098572 A1 | 7/2002 | Einerhand et al. | |
| 2002/0102714 A1 | 8/2002 | Wilson et al. | |
| 2003/0040101 A1 | 2/2003 | Wilson et al. | |
| 2003/0225260 A1 | 12/2003 | Snyder | |
| 2004/0014031 A1 | 1/2004 | Salvetti et al. | |
| 2005/0112765 A1 | 5/2005 | Li et al. | |
| 2007/0202587 A1 | 8/2007 | Hwang et al. | |
| 2008/0044855 A1 | 2/2008 | Xu et al. | |
| 2018/0155740 A1 | 6/2018 | Wu et al. | |
| 2018/0327722 A1 * | 11/2018 | Vink | C12N 7/00 |

FOREIGN PATENT DOCUMENTS

| | | |
|---|---|---|
| CN | 103189507 A | 7/2013 |
| EP | 1385946 B1 | 12/2009 |
| EP | 1797186 B1 | 5/2016 |
| GB | 2566572 A | 3/2019 |
| NZ | 528942 A | 3/2005 |
| WO | 9720943 A1 | 6/1997 |
| WO | 98/46728 A1 | 10/1998 |
| WO | 99/07833 A1 | 2/1999 |
| WO | 99/18227 A1 | 4/1999 |
| WO | 0017377 A2 | 3/2000 |
| WO | 03/061582 A2 | 7/2003 |
| WO | 2007127264 A2 | 11/2007 |
| WO | 2008063802 A2 | 5/2008 |
| WO | 2011123088 A1 | 10/2011 |
| WO | 2007148971 A2 | 9/2015 |
| WO | 2015137802 A1 | 9/2015 |
| WO | 2017/049759 A1 | 3/2017 |
| WO | 2017/149292 A1 | 9/2017 |
| WO | 2019141993 A1 | 7/2019 |
| WO | 2020161484 A1 | 8/2020 |

OTHER PUBLICATIONS

Altschul, et al., "Gapped BLAST and Psi-BLAST: A New Generation of Protein Database Search Programs", Nucleic Acids Res., 1997, vol. 25(17), pp. 3389-3402.
Boussif, O., et al., "A Versatile Vector for Gene and Oligonucleotide Transfer Into Cells in Culture and in Vivo: Polyethylenimine", Proc. Natl. Acad. Sci. USA, Aug. 1, 1995, vol. 92(16), pp. 7297-7301.
Ma, B., et al., "PatternHunter: Faster and More Sensitive Homology Search", Bioinformatics, Mar. 2002, vol. 18(3), pp. 440-445.
Ogasawara, Y., et al., "Efficient Production of Adeno-Associated Virus Vectors Using Split-type Helper Plasmids", Japanese Journal of Cancer Research, Apr. 1999, vol. 90(4), pp. 476-483.
Sitaraman, V., et al, "Computationally Designed Adeno-Associated Virus (AAV) Rep 78 is Efficiently Maintained Within an Adenovirus Vector", Proc. Natl. Acad. Sci. USA, Aug. 23, 2011, vol. 108(34), pp. 14294-14299.
Whiteway, A., et al., "Construction of Adeno-Associated Virus Packaging Plasmids and Cells that Directly Select for AAV Helper Functions", Journal of Virological Methods, 2003, vol. 114(1), pp. 1-10.

(Continued)

*Primary Examiner* — Bao Q Li
(74) *Attorney, Agent, or Firm* — McDonnell Boehnen Hulbert & Berghoff LLP

(57) ABSTRACT

The present invention relates to the production of plasmids which are useful in the production of Adeno-Associated Virus (AAV) particles. In particular, the invention provides nucleic acid molecules comprising capgenes and repgenes, wherein the capand repgenes are both operably-associated with the same promoter. The invention also provides host cells comprising nucleic acid molecules of the invention and methods for their use.

18 Claims, 10 Drawing Sheets
Specification includes a Sequence Listing.

(56) References Cited

OTHER PUBLICATIONS

Basic Local Alignment Search Tool. [Retrieved from the internet Mar. 4, 2017:<URL:http://www.ncbi.nlm.nih.gov/BLAST>].
"Searching the Trace Archive with Discontiguous MegaBlast". [Retrieved from the internet Mar. 4, 2019:<URL: www.ncbi.nlm.nih.gov/Web/Newsltr/FallWinter02/blastlab.html>].
International Search Report and Written Opinion, for International Application No. PCT/GB2019/050134, dated Mar. 21, 2019, pp. 1-15.
Search Report from the UK Intellectual Property Office, for Application No. GB1800903.5, dated Oct. 15, 2018, pp. 1-4.
Green, M.R. and Sambrook, J., "Molecular Cloning: A Laboratory Manual", Fourth Edition, 2012, vol. 1, pp. 1-34.
Clonetech—Helper Free System, 2016, pp. 1-22. [Retrieved from the internet on Jun. 8, 2020:<URL:www.clontech.com/GB/Products/Viral_Transduction/AAV_Vector_Systems/Helper_Free_Expression_System?sitex=10030:22372:US>].
Office Action dated Nov. 29, 2022 for Indian Patent Application No. 202047021768.
Alissa Bray et al., "Reconfiguration of AAV Rep-Cap Coding Sequences Significantly Increases Viral Vector Yield and Enables Inducible AAV Production in HEK293 Cells," European Society of Gene and Cell Therapy Annual Congress, Oct. 16-19, 2018.
Long-Sheng Chang et al., "The Adenovirus DNA-Binding Protein Stimulates the Rate of Transcription Directed by Adenovirus and Adeno-Associated Virus Promoters," J. Virology, vol. 64(5), pp. 2103-2109.

Bray, A., et al., "Reconfiguration of AAV Rep-Cap Coding Sequences Significantly Increase Viral Vector Yield and Enables Inducible AAV Production in HEK293 Cells", Poster presented at European Society of Gene Cell Therapy Annual Conference, Oct. 16-19, 2018.
Chahal, P., et al., "Key Rep-Proteins Necessary for the Adeno-Associated Virus Production by Transient Transfection in HEK293 Cells in Suspension and Serum-Free Medium", Molecular Therapy, May 1, 2018, vol. 26(5), Supplement 1, pp. 328, (Abstract only).
Gaillet, B., et al., "High-Level Recombinant Protein Production in CHO Cells Using Lentiviral Vectors and the Cumate Gene-Switch", Biotechnology and Bioengineering, Feb. 2010, vol. 106(2), pp. 203-215.
Hörner, M. and Weber, W., "Molecular Switches in Animal Cells", FEBS Letters, 2012, vol. 586, pp. 2084-2096.
International Search Report and Written Opinion from the International Searching Authority, for International Patent Application No. PCT/GB2020/050252, dated Mar. 18, 2020, pp. 1-17.
Mullick, A., et al., "The Cumate Gene-Switch: A System for Regulated Expression in Mammalian Cells ", BMC Biotechnology, Nov. 3, 2006, vol. 6(1), p. 43.
UK Search Report from the UK Intellectual Property Office, for GB1901571.8, dated Oct. 3, 2019, pp. 1-4.
"Introduction to Adeno-Associated Virus (AAV)", Vector Biolabs, article downloaded on Jan. 3, 2023 from https://www.vectorbiolabs.com/intro-to-aav/, 9 pages.
Notification of the First OA dated Dec. 28, 2022 issued in Chinese Patent Application No. 201980006731.8 and English Translation of Notification.

\* cited by examiner

US 11,697,824 B2

VECTOR FOR THE PRODUCTION OF AAV PARTICLES

CROSS-REFERENCE

This application is a 371 U.S. national phase of PCT/GB2019/050134, filed Jan. 18, 2019, which claims priority from GB patent application no. 1800903.5, filed Jan. 19, 2018, both which are incorporated by reference in its entirety.

FIELD OF THE INVENTION

The present invention relates to the production of plasmids which are useful in the production of Adeno-Associated Virus (AAV) particles. In particular, the invention provides nucleic acid molecules comprising cap genes and rep genes, wherein the cap and rep genes are both operably-associated with the same promoter. The invention also provides host cells comprising nucleic acid molecules of the invention and methods for their use.

BACKGROUND OF THE INVENTION

AAV vectors are developed from single-stranded DNA viruses that belong to the Parvoviridae family. This virus is capable of infecting a broad range of host cells, including both dividing and non-dividing cells. In addition, it is a non-pathogenic virus that generates only a limited immune response in most patients.

The AAV genome comprises two genes each encoding multiple open reading frames (ORFs): the rep gene encodes non-structural proteins that are required for the AAV life-cycle and site-specific integration of the viral genome; and the cap gene encodes the structural capsid proteins. In addition, these two genes are flanked by inverted terminal repeat (ITR) sequences consisting of 145 bases that have the ability to form hairpin structures. These hairpin sequences are required for the primase-independent synthesis of a second DNA strand and the integration of the viral DNA into the host cell genome.

In order to eliminate any integrative capacity of the virus, recombinant AAV vectors remove rep and cap from the DNA of the viral genome. To produce such vectors, the desired transgene(s), together with a promoter(s) to drive transcription of the transgene(s), is inserted between the inverted terminal repeats (ITRs); and the rep and cap genes are provided in trans in a second plasmid. A third plasmid, providing helper genes such as adenovirus E4, E2a and VA genes, is also used. All three plasmids are then transfected into cultured 'packaging' cells, such as HEK293.

Over the last few years, AAV vectors have emerged as an extremely useful and promising mode of gene delivery. This is owing to the following properties of these vectors:

AAVs are small, non-enveloped viruses and they have only two native genes (rep and cap). Thus they can be easily manipulated to develop vectors for different gene therapies.

AAV particles are not easily degraded by shear forces, enzymes or solvents. This facilitates easy purification and final formulation of these viral vectors.

AAVs are non-pathogenic and have a low immunogenicity. The use of these vectors further reduces the risk of adverse inflammatory reactions. Unlike other viral vectors, such as lentivirus, herpes virus and adenovirus, AAVs are harmless and are not thought to be responsible for causing any human disease.

Genetic sequences up to 4000 bp can be delivered into a patient using AAV vectors.

Whilst wild-type AAV vectors have been shown to sometimes insert genetic material into human chromosome 19, this property is generally eliminated from most AAV vectors by removing rep and cap genes from the viral genome. In such cases, the virus remains in an episomal form within the host cells. These episomes remain intact in non-dividing cells, while in dividing cells they are lost during cell division.

SUMMARY OF THE INVENTION

The inventors have recognised, however, that methods for the production of AAV vectors can be improved by optimising the ratios and amounts of the Rep and Cap proteins present during the vector-production process.

The present invention relates to the production of plasmids which are useful in the production of Adeno-Associated Virus (AAV) particles. In particular, the invention provides nucleic acid molecules comprising cap genes and rep genes, wherein the cap and rep genes are both operably-associated with the same promoter. The invention also provides host cells comprising nucleic acid molecules of the invention and methods for their use.

DESCRIPTION OF THE DRAWINGS

In FIG. 2B, "OXGP3" refers to a CMV promoter variant with two Tet operator sites.

In FIG. 4, the cell lysate containing the virus was diluted 500-fold and quantified using qPCR. This demonstrates the physical titre.

DETAILED DESCRIPTION OF THE INVENTION

It is an object of the invention, therefore, to provide a nucleic acid molecule which comprises cap and rep genes which are under the control of a single promoter; Cap and Rep polypeptides are thereby encoded within the same mRNA. The translation of the cap gene will be initiated by docking, at the ribosome, of a methylguanylate cap ($m^7G$) at the 5' terminal of the cap mRNA. Translation of the rep gene will be initiated by docking of a ribosome at an Internal Ribosome Entry Site (IRES) which is placed upstream of the rep gene.

Through the use of the nucleic acid molecules of the invention, higher virus titres may be obtained.

In some embodiments of the invention, the IRES replaces the wild-type p5 promoter. A further advantage of the removal of the p5 promoter is that, in the wild-type virus, the p5 promoter is bound by and is activated by the E2A DNA-binding protein (DBP). Hence the removal of the p5 promoter means that the E2A gene is not required (e.g. in a Helper Plasmid) to produce virus particles.

In one embodiment, the invention provides a nucleic acid molecule comprising:
  (i) a promoter,
  (ii) a cap gene, and
  (iii) a rep gene,
in the above 5'-3' order, wherein the cap gene and the rep gene are both operably-associated with the promoter, and wherein the rep gene is also operably-associated with an IRES.

The invention also provides a nucleic acid molecule comprising:
  (i) a cap gene, and
  (ii) a rep gene,
in the above 5'-3' order, wherein the rep gene is operably-associated with an IRES.

The nucleic acid molecule may be DNA or RNA, preferably DNA. The nucleic acid molecule may be single- or double-stranded, preferably double-stranded.

The nucleic acid molecule of the invention comprises a rep gene. As used herein, the term "rep gene" refers to a gene that encodes one or more open reading frames (ORFs), wherein each of said ORFs encodes an AAV Rep non-structural protein, or variant or derivative thereof. These AAV Rep non-structural proteins (or variants or derivatives thereof) are involved in AAV genome replication and/or AAV genome packaging.

Figure 1:
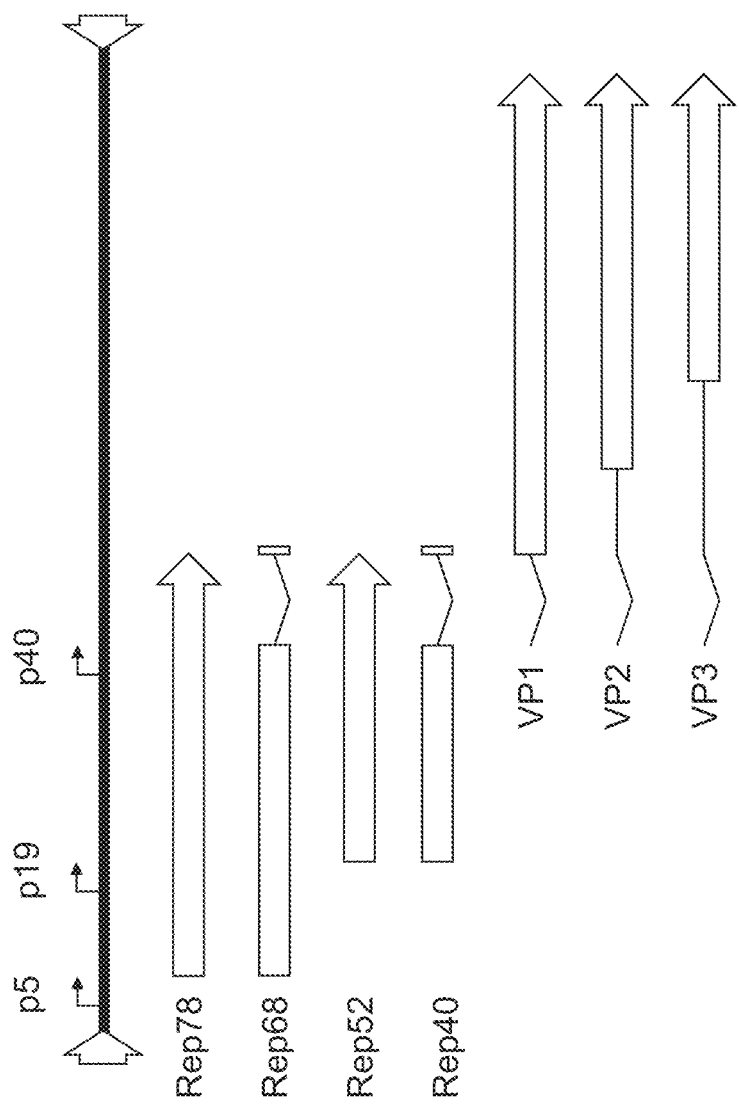
FIG. 1 shows the organisation of the Rep and Cap protein genes in the wild-type AAV genome.

The structure of the wild-type AAV genome, illustrating the organisation of the wild-type rep and cap genes, is shown in FIG. 1.

The wild-type rep gene comprises three promoters: p5, p19 and p40. Two overlapping messenger ribonucleic acids (mRNAs) of different lengths can be produced from p5 and from p19. Each of these mRNAs contains an intron which can be either spliced out or not using a single splice donor site and two different splice acceptor sites. Thus six different mRNAs can be formed, of which only four are functional. The two mRNAs that fail to remove the intron (one transcribed from p5 and one from p19) read through to a shared terminator sequence and encode Rep78 and Rep52, respectively. Removal of the intron and use of the 5'-most splice acceptor site does not result in production of any functional Rep protein—it cannot produce the correct Rep68 or Rep40 proteins as the frame of the remainder of the sequence is shifted, and it will also not produce the correct C-terminus of Rep78 or Rep52 because their terminator is spliced out. Conversely, removal of the intron and use of the 3' splice acceptor will include the correct C-terminus for Rep68 and Rep40, whilst splicing out the terminator of Rep78 and Rep52. Hence the only functional splicing either avoids splicing out the intron altogether (producing Rep78 and Rep52) or uses the 3' splice acceptor (to produce Rep68 and Rep40). Consequently four different functional Rep proteins with overlapping sequences can be synthesized from these promoters.

In the wild-type rep gene, the p40 promoter is located at the 3' end. Transcription of the Cap proteins (VP1, VP2 and VP3) is initiated from this promoter in the wild-type AAV genome.

The four wild-type Rep proteins are Rep78, Rep68, Rep52 and Rep40. Hence the wild-type rep gene is one which encodes the four Rep proteins Rep78, Rep68, Rep52 and Rep40.

Rep78 and 68 can specifically bind the hairpin formed by the ITR and cleave it at a specific region (i.e. the terminal resolution site) within the hairpin. In the wild-type virus, they are also necessary for the AAV-specific integration of the AAV genome. Rep 78 and Rep68 are transcribed under control of the p5 promoter in the wild type virus, and the difference between them reflects removal (or not) of an intron by splicing, hence they have different C terminal protein composition.

Rep52 and Rep40 are involved in genome packaging. Rep52 and Rep40 are transcribed under control of the p19 promoter in the wild type virus, and the difference between them reflects removal (or not) of an intron by splicing, hence they have different C terminal protein composition.

All four Rep proteins bind ATP and possess helicase activity. They up-regulate transcription from the p40 promoter, but down-regulate both p5 and p19 promoters.

As used herein, the term "rep gene" includes wild-type rep genes and derivatives thereof; and artificial rep genes which have equivalent functions.

In one embodiment, the rep gene encodes functional Rep78, Rep68, Rep52 and Rep40 proteins.

In a preferred example of this embodiment, Rep78 and Rep 68 are translated by ribosomes docking 5' to the Rep78 and Rep68 ATG start codon, thus allowing production of both of these proteins. In this example, the Rep78 and Rep68 open reading frames contain an active p40 promoter that provides the expression of both Rep52 and Rep40.

In some embodiments of the invention, the function of one or more of the p5, p19 and p40 promoters is removed/disabled, for example by codon-changing and/or removal of the TATA box, in order to prevent unwanted initiation of transcription from that promoter.

Preferably, the p5 promoter is non-functional (i.e. it cannot be used to initiate transcription). More preferably, the p5 promoter is replaced with the IRES (thus removing the function of the p5 promoter). This allows Rep78 or Rep68 to be transcribed in the same mRNA as the cap genes, but translation of the Rep78 and Rep68 proteins will be under the control of the IRES.

A further advantage of the removal of the p5 promoter is that, in the wild-type virus, the p5 promoter is bound by and is activated by the E2A DNA-binding protein (DBP). Hence the removal of the p5 promoter means that the E2A gene is not required (e.g. in a Helper Plasmid) to produce virus particles.

In one embodiment, the rep gene does not have a p5 promoter upstream. In another embodiment, the p5 promoter is not used in AAV packaging.

Preferably, the p19 promoter within the rep gene is functional.

In some embodiments, the function of the p40 promoter is removed/disabled within the Rep gene by one or more codon changes.

The cap gene is preferably relocated and its transcription is placed under control of an alternative promoter (e.g. CMV immediate early promoter).

There is a degree of redundancy between the function of the different Rep proteins and hence, in some embodiments of the invention, not all of the Rep proteins are required.

In some embodiments, the rep gene only encodes one, two, three or four of Rep78, Rep68, Rep52 and Rep40, preferably one, two or four of Rep78, Rep68, Rep52 and Rep40.

In some embodiments, the rep gene does not encode one or more of Rep78, Rep68, Rep52 and Rep40.

In some embodiments, the rep gene encodes Rep78 and Rep52, but does not encode Rep68 or Rep40. In this embodiment, the splice donor site remains in the DNA but both the 5' and 3' splice acceptor sites are removed. Hence the intron cannot be removed by splicing and transcription continues through to the terminator sequence for Rep78 and Rep52 (which is common to both). The Rep78 protein is transcribed in the same mRNA as the cap gene (hence is driven by the same promoter), and translation of Rep78 is driven by the IRES. Transcription of Rep52 is driven by the p19 promoter; hence it forms a separate mRNA and is translated by 5' m$^7$G cap-dependent docking at the ribosome. Accordingly, Rep68 and Rep40 cannot be produced in this embodiment.

In other embodiments, the rep gene encodes Rep68 and Rep40, but does not encode Rep78 or Rep52. In this embodiment, the intronic sequence between the splice donor and 3' splice acceptor is removed at the DNA level, placing the C terminus of Rep68 and Rep40 in frame with the upstream coding sequence. Hence Rep68 and Rep40 (but not Rep78 and Rep52) are produced. For clarity, Rep68 is transcribed in the same mRNA as the Cap proteins and it is translated under control of the IRES. In contrast, Rep40 is transcribed into a separate mRNA by the p19 promoter and it is translated by 5' m$^7$G cap docking at the ribosome.

In some embodiments, the rep gene encodes Rep78 and Rep68, but does not encode Rep52 or Rep40. This may be achieved by mutating the p19 promoter (e.g. inserting a mutation at the p19 TATA box).

In some embodiments, the rep gene encodes Rep52 and Rep40, but does not encode Rep78 or Rep68. This may be achieved by including just the coding sequence from the ATG of Rep52/40.

As used above, the term "encodes" means that the rep gene encodes a functional form of that Rep protein. Similarly, the term "does not encode" means that the rep gene does not encode a functional form of that Rep protein.

In the absence of sufficient Rep proteins, lower titres (e.g. genome copies) would be observed (which could be determined by qPCR), due to the fact that there is less ITR plasmid to be packaged and that it would not be effectively packaged. The observation might also include an exaggerated empty:full particle ratio; this could be determined by ELISA or optical density measurement.

The wild-type AAV (serotype 2) rep gene nucleotide sequence is given in SEQ ID NO: 1. The wild-type AAV (serotype 2) Rep78, Rep68, Rep52 and Rep40 amino acid sequences are given in SEQ ID NOs: 2, 3, 4 and 5, respectively. The wild-type AAV (serotype 2) nucleotide sequence encoding Rep78 is given in SEQ ID NO: 6. The wild-type AAV (serotype 2) nucleotide sequence encoding Rep68 is given in SEQ ID NO: 7. The wild-type AAV (serotype 2) nucleotide sequence encoding Rep52 is given in SEQ ID NO: 8. The wild-type AAV (serotype 2) nucleotide sequence encoding Rep 40 is given in SEQ ID NO: 9.

In one embodiment, the term "rep gene" refers to a nucleotide sequence having at least 70%, 80%, 85%, 90%, 95%, 99% or 100% sequence identity to SEQ ID NO: 1 and which encodes one or more Rep78, Rep68, Rep52 and Rep40 polypeptides.

In another embodiment, the term "rep gene" refers to a nucleotide sequence having at least 70%, 80%, 85%, 90%, 95%, 99% or 100% sequence identity to SEQ ID NO: 6 and which encodes functional Rep78 and/or Rep52 polypeptides (and preferably does not encode functional Rep68 or Rep40 polypeptides).

In another embodiment, the term "rep gene" refers to a nucleotide sequence having at least 70%, 80%, 85%, 90%, 95%, 99% or 100% sequence identity to SEQ ID NO: 7 and which encodes functional Rep68 and/or Rep40 polypeptides (and preferably does not encode functional Rep78 or Rep52 polypeptides).

In another embodiment, the term "rep gene" refers to a nucleotide sequence having at least 70%, 80%, 85%, 90%, 95%, 99% or 100% sequence identity to SEQ ID NO: 8 and which encodes a functional Rep52 polypeptide (and preferably does not encode a functional Rep78 polypeptide).

In another embodiment, the term "rep gene" refers to a nucleotide sequence having at least 70%, 80%, 85%, 90%, 95%, 99% or 100% sequence identity to SEQ ID NO: 9 and which encodes a functional Rep40 polypeptide (and preferably does not encode functional Rep68 polypeptide).

In another embodiment, the term "rep gene" refers to a nucleotide sequence having at least 90%, 95%, 99% or 100% sequence identity to a nucleotide sequence which encodes SEQ ID NO: 2 and which encodes functional Rep78 and/or Rep52 polypeptides (and preferably does not encode functional Rep68 or Rep40 polypeptides).

In another embodiment, the term "rep gene" refers to a nucleotide sequence having at least 90%, 95%, 99% or 100% sequence identity to a nucleotide sequence which encodes SEQ ID NO: 3 and which encodes functional Rep68 and/or Rep40 polypeptides (and preferably does not encode functional Rep78 or Rep52 polypeptides).

In another embodiment, the term "rep gene" refers to a nucleotide sequence having at least 90%, 95%, 99% or 100% sequence identity to a nucleotide sequence which encodes SEQ ID NO: 4 and which encodes a functional Rep52 polypeptide (and preferably does not encode a functional Rep78 polypeptide).

In another embodiment, the term "rep gene" refers to a nucleotide sequence having at least 90%, 95%, 99% or 100% sequence identity to a nucleotide sequence which encodes SEQ ID NO: 5 and which encodes a functional Rep40 polypeptide (and preferably does not encode functional Rep68 polypeptide).

In some embodiments, the nucleic acid molecule of the invention does not encode a functional Rep78 polypeptide. In some embodiments, the nucleic acid molecule of the invention does not encode a functional Rep68 polypeptide. In some embodiments, the nucleic acid molecule of the invention does not encode a functional Rep52 polypeptide. In some embodiments, the nucleic acid molecule of the invention does not encode a functional Rep40 polypeptide.

The nucleic acid molecule also comprises a cap gene. As used herein, the term "cap gene" refers to a gene that encodes one or more open reading frames (ORFs), wherein each of said ORFs encodes an AAV Cap structural protein, or variant or derivative thereof. These AAV Cap structural proteins (or variants or derivatives thereof) form the AAV capsid.

The three Cap proteins must function to enable the production of an infectious AAV virus particle which is capable of infecting a suitable cell. The three Cap proteins are VP1, VP2 and VP3, which are generally 87 kDa, 72 kDa and 62 kDa in size, respectively. Hence the cap gene is one which encodes the three Cap proteins VP1, VP2 and VP3.

In the wild-type AAV, these three proteins are translated from the p40 promoter to form a single mRNA. After this mRNA is synthesized, either a long or a short intron can be excised, resulting in the formation of a 2.3 kb or a 2.6 kb mRNA.

Usually, especially in the presence of adenovirus, the long intron is excised. In this form the first AUG codon, from which the synthesis of VP1 protein starts, is cut out, resulting in a reduced overall level of VP1 protein synthesis. The first AUG codon that remains is the initiation codon for VP3 protein. However, upstream of that codon in the same open reading frame lies an ACG sequence (encoding threonine) which is surrounded by an optimal Kozak context. This contributes to a low level of synthesis of VP2 protein, which is actually VP3 protein with additional N terminal residues, as is VP1.

If the long intron is spliced out, and since in the major splice the ACG codon is a much weaker translation initiation signal, the ratio at which the AAV structural proteins are synthesized in vivo is about 1:1:10, which is the same as in the mature virus particle. The unique fragment at the N-terminus of VP1 protein has been shown to possess phospholipase A2 (PLA2) activity, which is probably required for the releasing of AAV particles from late endosomes.

The AAV capsid is composed of 60 capsid protein subunits (VP1, VP2, and VP3) that are arranged in an icosahedral symmetry in a ratio of 1:1:10, with an estimated size of 3.9 MDa.

As used herein, the term "cap gene" includes wild-type cap genes and derivatives thereof, and artificial cap genes which have equivalent functions. The AAV (serotype 2) cap gene nucleotide sequence and Cap polypeptide sequences are given in SEQ ID NOs: 10 and 11, respectively.

As used herein, the term "cap gene" refers preferably to a nucleotide sequence having the sequence given in SEQ ID NO: 10 or a nucleotide sequence encoding SEQ ID NO: 11; or a nucleotide sequence having at least 70%, 80%, 85%, 90%, 95% or 99% sequence identity to SEQ ID NO: 10 or at least 80%, 90%, 95% or 99% nucleotide sequence identity to a nucleotide sequence encoding SEQ ID NO: 11, and which encodes VP1, VP2 and VP3 polypeptides.

The rep and cap genes are preferably viral genes or derived from viral genes. More preferably, they are AAV genes or derived from AAV genes. In some embodiments, the AAV is an Adeno-associated dependoparvovirus A. In other embodiments, the AAV is an Adeno-associated dependoparvovirus B.

11 different AAV serotypes are known. All of the known serotypes can infect cells from multiple diverse tissue types. Tissue specificity is determined by the capsid serotype.

The AAV may be from serotype 1, 2, 3, 4, 5, 6, 7, 8, 9, 10 or 11. Preferably, the AAV is serotype 1, 2, 5, 6, 7 or 8. Most preferably, the AAV serotype is 2 (i.e. AAV2).

The rep and cap genes (and each of the protein-encoding ORFs therein) may be from one or more different viruses (e.g. 2, 3 or 4 different viruses). For example, the rep gene may be from AAV2, whilst the cap gene may be from AAV5. It is recognised by those in the art that the rep and cap genes of AAV vary by clade and isolate. The sequences of these genes from all such clades and isolates are encompassed herein, as well as derivatives thereof.

The cap gene and rep gene are present in the nucleic acid in this 5'→3' order. However, since Rep52 and/or Rep40 may be transcribed from their own p19 promoter, the position of the coding sequence which encodes Rep52 and/or Rep40 may be varied. For example, the coding sequence which encodes Rep52 and/or Rep40 may be placed upstream or downstream of the cap genes and rep genes which encode Rep78/68; or indeed on the reverse strand of the nucleic acid of the invention or on a different nucleic acid.

The cap and rep genes are both operably-associated with the same promoter. The promoter is preferably 5' (i.e. upstream) of the cap and rep genes. In some embodiments, the promoter is a constitutive promoter. In other embodiments, the promoter is inducible or repressible.

Examples of constitutive promoters include the CMV, SV40, PGK (human or mouse), HSV TK, SFFV, Ubiquitin, Elongation Factor Alpha, CHEF-1, FerH, Grp78, RSV, Adenovirus E1A, CAG or CMV-Beta-Globin promoter, or a promoter derived therefrom. Preferably, the promoter is the cytomegalovirus immediate early (CMV) promoter, or a promoter which is derived therefrom, or a promoter of equal or increased strength compared to the CMV promoter in human cells and human cell lines (e.g. HEK-293 cells).

In some embodiments, the promoter is inducible or repressible by the inclusion of an inducible or repressible regulatory (promoter) element. For example, the promoter may one which is inducible with doxycycline, tetracycline, IPTG or lactose.

Preferably, the inducible promoter element comprises a plurality of Tet operator sequences to which the Tet repressor protein (TetR) is capable of binding. In the bound state, tight suppression of transcription is obtained. However, in the presence of doxycycline (or less preferably, tetracycline), suppression is alleviated, thus allowing the promoter to gain full transcriptional activity. Such an inducible promoter element is preferably placed downstream of another promoter, e.g. the CMV promoter.

The TetR binding site may have a wild-type sequence, many of which are known in the art. Preferably, the TetR binding site has been subject to one or more improvements by incorporating minor sequence changes. A preferred version that may be used in an embodiment of the invention has the sequence tccctatcagtgatagaga (SEQ ID NO: 12).

Alternative versions of the repressor element that bind the TetR protein or derivatives of the TetR protein may also be used in an embodiment of the invention provided that the TetR repressor protein binds to the TetR binding sequence variant used. Some repressor/binding site variants will have higher than wild-type affinity for each other; these are preferable in an embodiment of the invention.

The TetR gene will generally be integrated into the chromosome of a human (host) cell. The gene may or may not be integrated adjacent to, or in conjunction with, the cap or rep genes. In some embodiments, the TetR gene is co-expressed with the cap gene or rep gene.

In one embodiment of the invention, the nucleotide sequence of the TetR protein is as given in SEQ ID NO: 13 or a nucleotide sequence having at least 80%, more preferably at least 85%, 90% or 95% sequence identity thereto and which codes for a TetR protein.

In another embodiment of the invention, the amino acid sequence of the TetR protein is as given in SEQ ID NO: 14 or an amino acid sequence having at least 80%, more preferably at least 85%, 90% or 95% sequence identity thereto and which encodes a TetR protein.

Preferably, the promoter which is operably-associated with the cap and rep genes is the CMV immediate early promoter or a derivative thereof. In some particularly-preferred embodiments, the promoter is a promoter as defined in WO2017/149292 (more preferably, a promoter as defined therein as "p565"). Preferably, the promoter which is operably-associated with the cap and rep genes is not an AAV promoter, e.g. it is not an AAV p5, p19 or p40 promoter.

Translation of the cap gene is preferably initiated from the standard 5' $m^7G$-cap at the 5' end of the m RNA.

The rep gene is also operably-associated with an Internal Ribosome Entry Site (IRES). The IRES regulates the translation of the rep mRNA. IRESs are distinct regions of nucleic acid molecules that are able to recruit eukaryotic ribosomes to the mRNA in a process which is known as cap-independent translation. IRESs are commonly located in the 5'-UTRs of RNA viruses. They facilitate translation of the viral RNAs in a cap-independent manner.

Examples of viral IRESs include Picornavirus IRES (Encephalomyocarditis virus, EMCV IRES), Aphthovirus IRES (Foot-and-mouth disease virus, FMDV IRES), Kaposi's sarcoma-associated herpes virus IRES, Hepatitis A IRES, Hepatitis C IRES, Pestivirus IRES, Cripavirus internal ribosome entry site (IRES), *Rhopalosiphum padi* virus internal ribosome entry site (IRES) and 5'-Leader IRES and intercistronic IRES in the 1.8-kb family of immediate early transcripts (IRES)1.

The invention also encompasses non-natural derivatives of the above IRESs which retain the capacity to recruit eukaryotic ribosomes to the mRNA. In some preferred embodiments, the IRES is an encephalomyocarditis virus (EMCV) IRES. In one embodiment of the invention, the nucleotide sequence of the EMCV IRES is as given in SEQ ID NO: 15 or a nucleotide sequence having at least 80%, more preferably at least 85%, 90% or 95% sequence identity thereto and which encodes an IRES.

In other embodiments, the IRES is a Foot-and-mouth disease virus (FMDV) IRES. In one embodiment of the invention, the nucleotide sequence of the FMDV IRES is as given in SEQ ID NO: 16 or a nucleotide sequence having at least 80%, more preferably at least 85%, 90% or 95% sequence identity thereto and which encodes an IRES.

The rep gene is operably-associated with the IRES. Preferably, the IRES is located downstream of the cap gene and upstream of the translation start site for Rep 78/68.

The production of stable cell lines in mammalian culture typically requires a method of selection to promote the growth of cells containing any exogenously-added DNA. Preferably, the nucleic acid molecules of the invention additionally comprise a selection gene or an antibiotic resistance gene. To this end, a range of genes are known that provide resistance to specific compounds when the DNA encoding them is inserted into a mammalian cell genome.

Preferably, the selection gene is puromycin N-acetyl-transferase (Puro), hygromycin phosphotransferase (Hygro), blasticidin s deaminase (Blast), Neomycin phosphotransferase (Neo), glutathione S-transferase (GS), zeocin resistance gene (Sh ble) or dihydrofolate reductase (DHFR). Each of these genes provides resistance to a small molecule known to be toxic to mammalian cells, or in the case of GS provides a method for cells to generate glutathione in the absence of glutathione in the growth media.

In a preferred embodiment of the invention, the resistance gene is Puro. This gene is particularly effective because many of the cell lines used in common tissue culture are not resistant to Puro; this cannot be said for Neo where many, particularly HEK 293 derivatives, are already Neo resistant due to previous genetic manipulations by researchers (e.g. HEK 293T cells). Puro selection also has the advantage of being toxic over a short time window (<72 hours), and hence it allows variables to be tested rapidly and cells that do not harbour the exogenous DNA to be inserted into the genome are rapidly removed from the culture systems. This cannot be said of some other selection methods such as Hygro, where toxicity is much slower onset.

The development of stable cell lines using selection genes (e.g. Puro) requires that the resistance gene must be expressed in the cells. This can be achieved through a variety of methods including, but not limited to, internal ribosome entry sites (IRES), 2A cleavage systems, alternative splicing, and dedicated promoters.

In a preferred embodiment of the invention, the selection gene will be expressed from a dedicated promoter. This promoter will preferably transcribe in human cells at lower levels than the dedicated promoters driving the rep or cap genes.

Each of the genes in the nucleic acid molecule which encode a polypeptide or RNA will preferably be operably-associated with one or more regulatory elements. This ensures that the polypeptide or RNA is expressed at the desired level and at the desired time. In this context, the term "regulatory elements" includes one or more of an enhancer, promoter, intron, polyA, insulator or terminator.

The genes used in the AAV plasmids or vectors disclosed herein are preferably separated by polyA signals and/or insulators in an effort to keep transcriptional read-through to other genes to a minimum.

While some advantages may be obtained by using copies of the same regulatory element (e.g. promoter sequence) with more than one polypeptide or RNA-encoding nucleotide sequence (in terms of their co-ordinated expression), in the context of this invention, it is highly desirable to use different regulatory elements with each polypeptide or RNA-encoding nucleotide sequence.

Preferably, therefore, the rep and cap genes are operably-associated with different regulatory elements, e.g. different promoter, different intron, different polyA, different insulator and/or different terminator sequences. More preferably, the degree of nucleotide sequence identity between the rep promoter and the cap promoter is less than 95% or less than 90%, more preferably less than 85%, 80%, 70% or 60%. More preferably, the degree of nucleotide sequence identity between the rep terminator and the cap terminator is less than 95% or less than 90%, more preferably less than 85%, 80%, 70% or 60%. In this way, the risk of homologous recombination between these regulatory elements is reduced.

The nucleic acid molecule of the invention will, most embodiments, be a plasmid or vector which is useful in the production of AAVs. In most embodiments, therefore, the nucleic acid molecule of the invention (or the vector or plasmid comprising it) will not comprise inverted terminal repeats (ITRs).

In some embodiments, the nucleic acid molecule of the invention (or the vector or plasmid comprising it) will not comprise one or more genes selected from Adenovirus E1A, E1B, E4, E2A or VA. In some preferred embodiments, the nucleic acid molecule of the invention (or the vector or plasmid or plasmid system comprising it) does not comprise the Adenovirus E2A gene. As used herein, the term "E2A" or "E2A gene" refers to a viral E2A gene or a variant or derivative thereof. Preferably, the E2A gene is from or derived from a human adenovirus, e.g. Ad5. In one embodiment of the invention, the nucleotide sequence of the Adenovirus E2A gene is as given in SEQ ID NO: 17 or a nucleotide sequence having at least 80%, more preferably at least 85%, 90% or 95% sequence identity thereto and which encodes a DNA-binding protein which aids elongation of viral DNA replication.

In another embodiment, there is provided a plasmid or vector comprising a nucleic acid molecule of the invention.

Examples of preferred embodiments of the invention include nucleic acid molecules comprising the following elements in this order:

CMV promoter—AAV2 cap gene—FMDV IRES—rep gene p565 promoter—AAV2 cap gene—EMCV IRES—rep gene CMV promoter—AAV2 cap gene—EMCV IRES—rep gene In some preferred embodiments, the "rep gene" refers to a gene which encodes Rep78, Rep52, Rep68 and Rep40 polypeptides. In other preferred embodiments, the term "rep gene" refers to a gene which encodes Rep78 and Rep52 polypeptides (but preferably does not encode functional Rep68 or Rep40 polypeptides).

There are many established algorithms available to align two amino acid or nucleic acid sequences. Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid or nucleic acid sequences for comparison may be conducted, for example, by computer-implemented algorithms (e.g. GAP, BESTFIT, FASTA or TFASTA), or BLAST and BLAST 2.0 algorithms.

Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402; and http://www.ncbi.nlm.nih.gov/BLAST). Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used.

With regard to nucleotide sequence comparisons, MEGABLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention.

The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page (www.ncbi.nlm.nih.gov/Web/Newsltr/FallWinter02/blast-lab.html). This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are: word size: 11 or 12; template: 16, 18, or 21; template type: coding (0), non-coding (1), or both (2).

In some embodiments, the BLASTP 2.5.0+ algorithm may be used (such as that available from the NCBI) using the default parameters. In other embodiments, a BLAST Global Alignment program may be used (such as that available from the NCBI) using a Needleman-Wunsch alignment of two protein sequences with the gap costs: Existence 11 and Extension 1.

One method for the production of recombinant AAVs is based on the transient transfection of all elements that are required for AAV production into host cells, such as HEK293 cells. This generally involves the co-transfection of AAV production cells with 3 plasmids:

(a) an AAV ITR-containing plasmid, carrying the gene of interest;
(b) a plasmid that carries the AAV rep-cap genes; and
(c) a plasmid that provides the necessary helper genes isolated from adenovirus.

In some instances, the helper genes are stably integrated into (and expressible from) the host cell genome; therefore plasmid (c) is not needed.

The invention therefore provides a kit comprising:
(a) a plasmid or vector comprising a nucleic acid molecule of the invention, together with one or more of the following—
(b) an AAV Transfer Plasmid comprising a transgene flanked by ITRs;
(c) a Helper Plasmid comprising one or more genes selected from Adenovirus E1A, E1B, E4 and VA.

In some embodiments of the invention, the Helper Plasmid additionally comprises an E2A gene. In other embodiments, the Helper Plasmid does not comprise an E2A gene. In the latter case, the omission of the E2A gene reduces considerably the amount of DNA which is needed in the Helper Plasmid.

The invention also provides a kit comprising:
(a) a plasmid or vector comprising a nucleic acid molecule of the invention, together with one or more of the following—
(b) an AAV Transfer Plasmid comprising a transgene flanked by ITRs;
(c) a mammalian host cell (e.g. HEK293) comprising one or more viral genes selected from E1A, E1B, E4 and VA expressible from the host cell genome.

In some embodiments of the invention, the mammalian host cell additionally comprises an E2A gene expressible from the host cell genome. In other embodiments, the mammalian host cell does not comprise an Adenovirus E2A gene.

The kit may also contain materials for purification of the AAV particles such as those involved in the density banding and purification of viral particles, e.g. one or more of centrifuge tubes, Iodixanol, dialysis buffers and dialysis cassettes.

The invention also provides a mammalian cell comprising a nucleic acid molecule, plasmid or vector of the invention. The nucleic acid molecule of the invention may be stably integrated into the nuclear genome of the mammalian cell or present within a vector or plasmid (e.g. episome) within the cell.

Preferably, the nucleic acid molecule of the invention is stably integrated into the nuclear genome of the mammalian cell (and wherein the rep and cap genes are expressible therefrom).

The cells may be isolated cells, e.g. they are not situated in a living animal or mammal. Examples of mammalian cells include those from any organ or tissue from humans, mice, rats, hamsters, monkeys, rabbits, donkeys, horses, sheep, cows and apes. Preferably, the cells are human cells. The cells may be primary or immortalised cells.

Preferred cells include HEK-293, HEK 293T, HEK-293E, HEK-293 FT, HEK-293S,

HEK-293SG, HEK-293 FTM, HEK-293SGGD, HEK-293A, MDCK, C127, A549, HeLa, CHO, mouse myeloma, PerC6, 911 and Vero cell lines. HEK-293 cells have been modified to contain the E1A and E1B proteins and this obviates the need for these proteins to be supplied on a Helper Plasmid. Similarly, PerC6 and 911 cells contain a similar modification and can also be used. Most preferably, the human cells are HEK293, HEK293T, HEK293A, PerC6 or 911. Other preferred cells include CHO and VERO cells.

Preferably, the cells of the invention are capable of inducibly expressing the rep and cap genes.

The invention also provides an AAV packaging cell, preferably a mammalian cell, more preferably a human cell), comprising (a) a nucleic acid molecule of the invention, and optionally one or both of (b) an AAV Transfer Plasmid comprising a transgene flanked by ITRs, and (c) a Helper Plasmid comprising one or more genes selected from E1A, E1B, E4 and VA. In some embodiments of the invention, the Helper Plasmid additionally comprises an E2A gene. In other embodiments, the Helper Plasmid does not comprise an E2A gene. In the latter case, the omission of the E2A gene reduces considerably the amount of DNA which is needed in the Helper Plasmid.

The nucleic acid molecules, plasmids and vectors of the invention may be made by any suitable technique. Recombinant methods for the production of the nucleic acid molecules and packaging cells of the invention are well known in the art (e.g. "Molecular Cloning: A Laboratory Manual" (Fourth Edition), Green, M R and Sambrook, J., (updated 2014)).

The expression of the rep and cap genes from the nucleic acid molecules of the invention may be assayed in any suitable assay, e.g. by assaying for the number of genome copies per ml by qPCR (as described the Examples herein).

In a further embodiment, there is provided a process for producing an AAV packaging cell, the process comprising the steps:
(a) stably integrating a nucleic acid molecule of the invention into a mammalian cell, thereby producing a mammalian cell that expresses viral rep and cap genes.

The invention also provides the use of an AAV packaging cell of the invention in the production of an AAV particle.

The invention also provides a process for producing AAVs, the process comprising the steps:
(a) introducing a Transfer Plasmid comprising 5'—and 3'-AAV ITRs flanking a transgene into an AAV packaging cell, the AAV packaging cell comprising a nucleic acid molecule of the invention and sufficient helper genes (preferably selected from one or more of E1A, E1B, E4 and VA) for packaging the Transfer Plasmid, the helper genes either being present in an episomal Helper Plasmid within the cell or being integrated into the packaging cell genome;
(b) culturing the cell under conditions such that AAVs are assembled and secreted by the cell; and
(c) harvesting packaged AAVs from the supernatant.

In some embodiments of the invention, the helper genes additionally include an E2A gene. In other embodiments, the helper genes do not include an E2A gene.

Preferably, the harvested AAVs are subsequently purified.

As used herein, the term "introducing" one or more plasmids or vectors into the cell includes transformation, and any form of electroporation, conjugation, infection, transduction or transfection, inter alia.

In some preferred embodiments, the transgene encodes a CRISPR enzyme (e.g. Cas9, Cpf1) or a CRISPR sgRNA.

Processes for such introduction are well known in the art (e.g. Proc. Natl. Acad. Sci. USA. 1995 Aug. 1; 92 (16): 7297-301).

The disclosure of each reference set forth herein is specifically incorporated herein by reference in its entirety.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Production of AAV Cap-Rep Plasmids

Figure 2A:
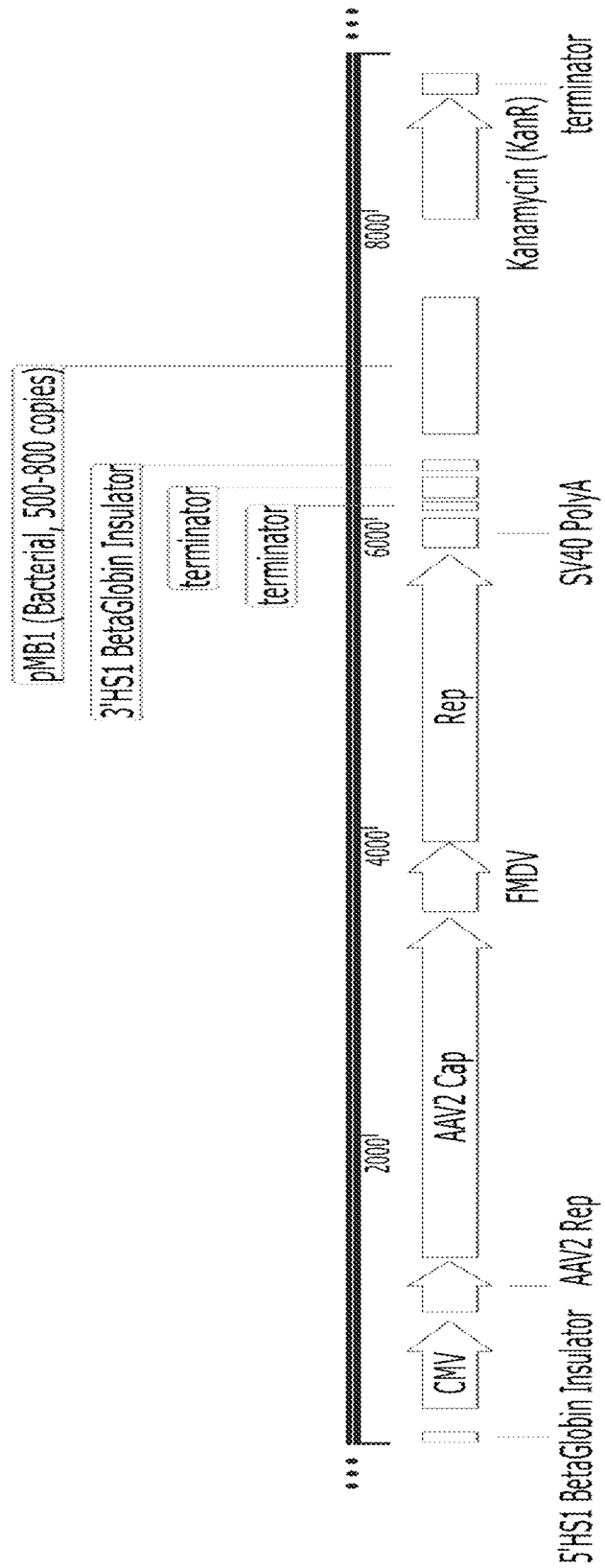
FIGS. 2A, 2B and 2C show three embodiments of the nucleic acid molecule of the invention.
Figure 2B:
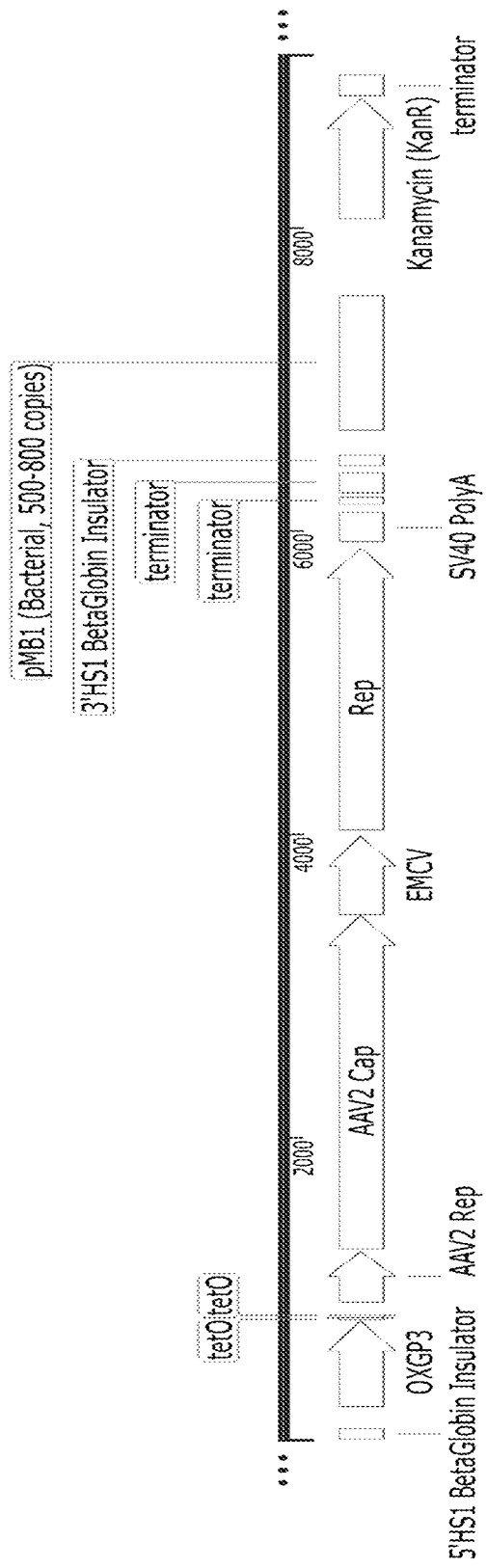
Figure 2C:
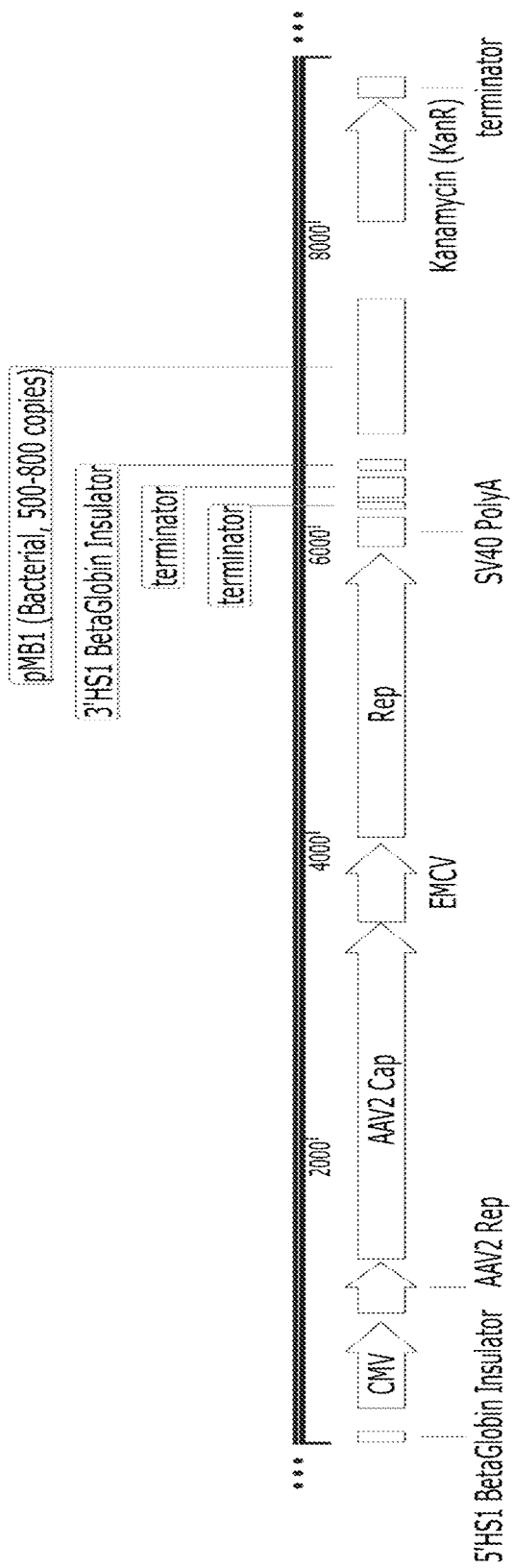

The following plasmids were produced having the genetic elements as shown in FIGS. 2A, 2B, and 2C:
pSF-CMV-AAV2Cap-FMDV-AAV2Rep
pSF-CMV-AAV2Cap-EMCV-AAV2Rep
pSF-p565_2×TetO-AAV2Cap-EMCV-AAV2Rep The OxGP3 promoter is the p565 promoter as defined in WO2017/149292. FMDV is the Foot and Mouth Disease Virus IRES. CMV is the CytoMegaloVirus promoter. AAV2Cap is the Adeno-Associated Virus 2 cap gene. Rep is the Adeno-Associated Virus rep gene encoding Rep78 and Rep52 only.

pSF-AAV-CMV-EGFP

This plasmid encodes an EGFP protein driven by the CMV promoter, flanked by two AAV2 ITR sequences to allow the packaging of the ITR-CMV-EGFP-ITR sequence into the AAV capsid shell.

pSF-Helper

This plasmid contains Adenovirus 5 sequences E2A, E4orf6 and VAI RNA, to provide the helper functions required for AAV production in HEK293 cells.

pSF-RepCap

This plasmid contains the RepCap sequences in the wild-type configuration, with the p5 promoter removed and placed distally to lower the overall expression of Rep78/68.

pSF-CMV-Cap-CMV-Rep78/52

This plasmid contains the Cap sequence driven by a CMV and the Rep78/52 sequence separately driven by a CMV promoter. This gives equally strong expression of the two coding sequences.

pSF-CMV-Cap-PGK-Rep78/52

This plasmid contains the Cap sequence driven by a CMV and the Rep78/52 sequence separately driven by a PGK promoter, which gives lower expression than the CMV promoter.

pSF-CMV-Cap-EMCV-Rep78/52

This plasmid contains the Cap sequence driven by a CMV promoter, and the Rep78/52 protein produced from the IRES EMCV. The EMCV gives much lower expression levels than the CMV promoter.

Example 2: Assaying for Genome Copies (GC)

Figure 3:
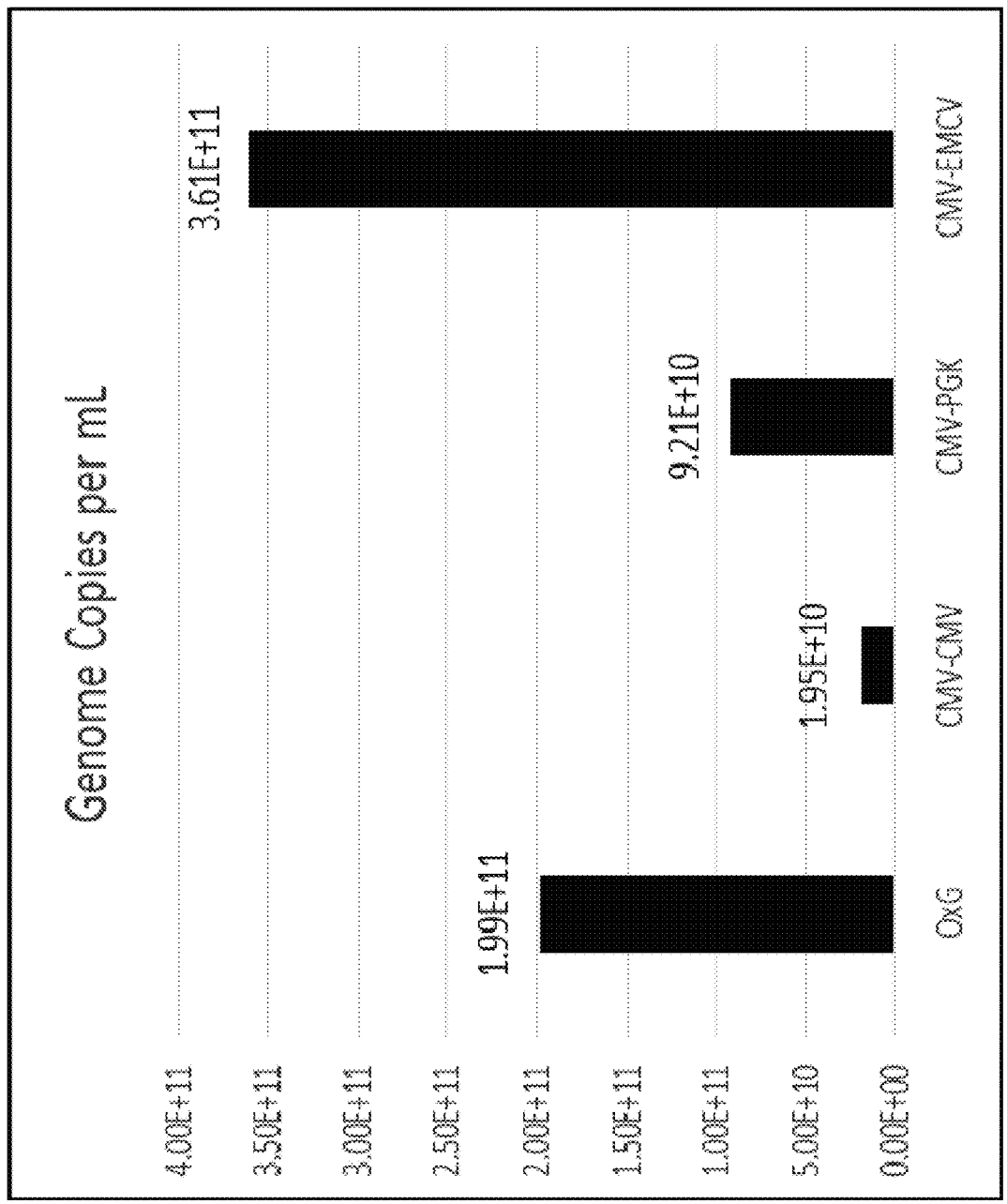
FIGS. 3-4 show the results of assays for the number of copies of the AAV genome per ml which were produced in cells transfected with various rep-cap plasmids. OxG=a standard RepCap configuration as found in the wild-type virus, including the p5 promoter which was placed distally; CMV-CMV=a configuration in which both Rep and Cap sequences were placed under CMV promoters, in the 5'-3' order CMV-Cap-CMV-Rep; CMV-PGK=a configuration in which Rep and Cap sequences were placed under PGK and CMV promoters respectively, in the 5'-3' order CMV-Cap-PGK-Rep; CMV-EMCV=a configuration in which Cap sequences were placed under the CMV promoter and Rep sequence placed under the control of the IRES EMCV, in the 5'-3' order CMV-Cap-EMCV-Rep.
Figure 4:
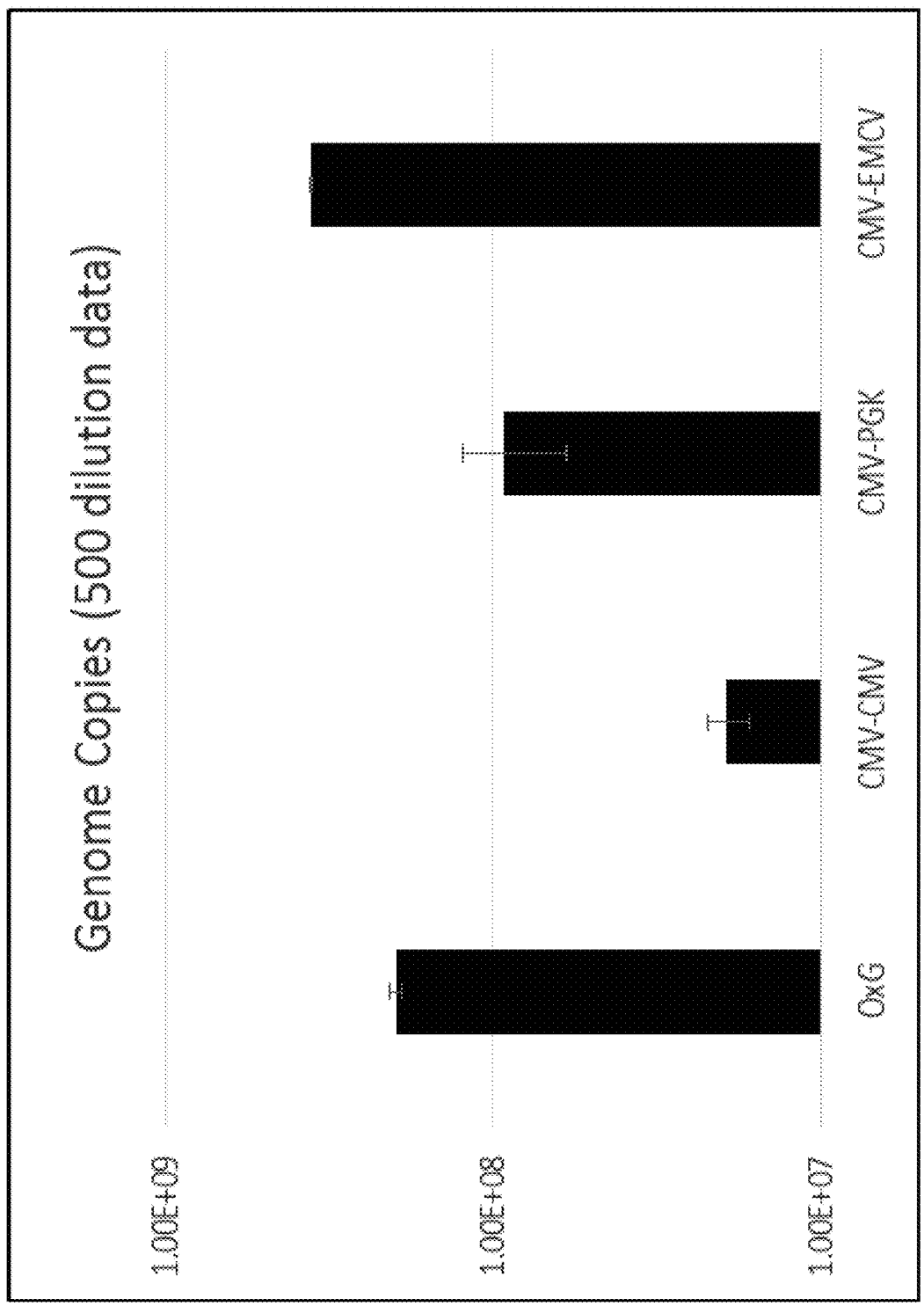
Figure 6:
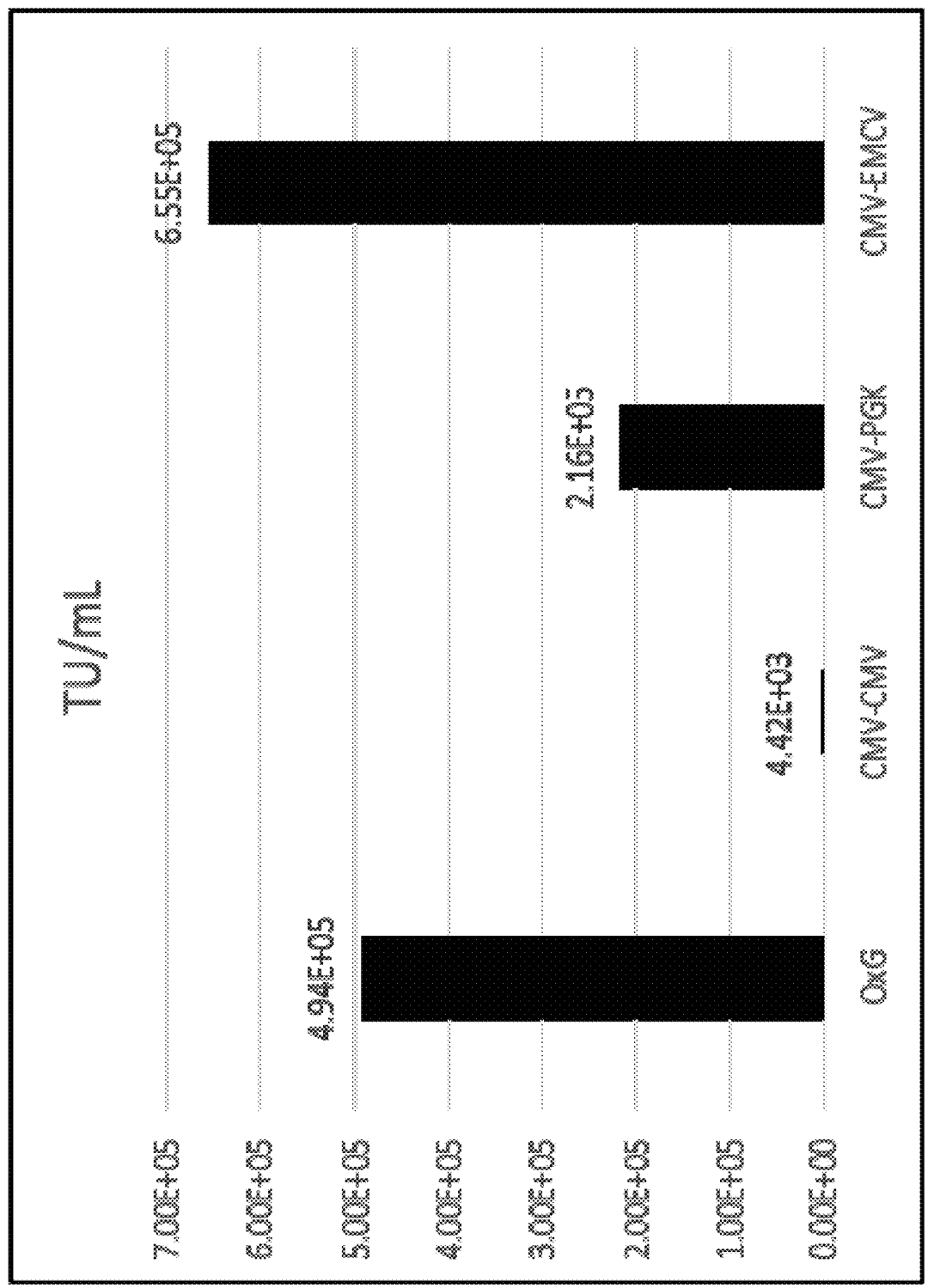
FIG. 6 shows the transducing units per millilitre of virus sample infected, as calculated by the results from FIG. 5 and the number of cells infected. This demonstrates the infectious titre.

Plasmid vectors pSF-AAV-CMV-EGFP, pSF-Helper and one of: pSF-RepCap; pSF-CMV-Cap-CMV-Rep78/52; pSF-CMV-Cap-PGK-Rep78/52 or pSF-CMV-Cap-EMCV-Rep78/52 were transfected in a 1:1:1 molar ratio into >80% confluent HEK293T cells in a 6-well plate, to a total of 2.5 µg of DNA per well. Transfection reagent Lipofectamine 2000 was used in a 1:2.4 ratio of total DNA mass to Lipofectamine. Entire well contents were harvested at 48 hours for analysis by both flow cytometry and qPCR. Data is presented as both the Transducing Units (TU) per mL of lysate (FIG. 6) and genome copies per mL of lysate (FIGS. 3-4).

By using the plasmid pSF-CMV-Cap-EMCV-Rep78/52, both the infectious and physical titre was improved compared to the wild-type configuration used in the OxG positive control.

Figure 5:
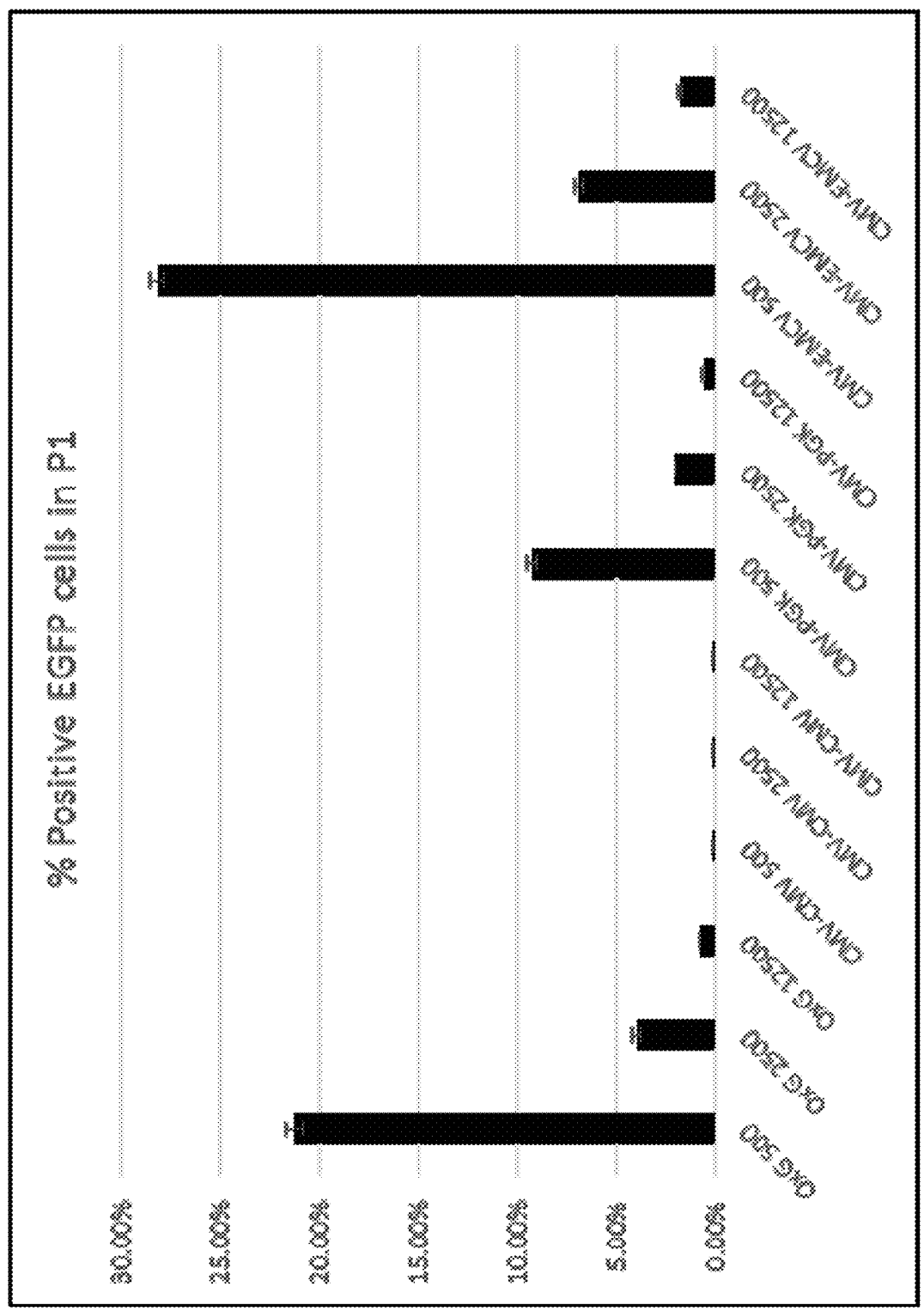
FIG. 5 shows the results following flow cytometry analysis of HEK293T cells 72 hours post infection with AAV particles. Data is given as a percentage of the GFP positive cells in P1. P1 corresponds to the viable cells in the sample.

FIG. 5 shows the percentage of viable cells which are GFP positive after 72 hours incubation with AAV. The viral solution was diluted to 1 in 500, 1 in 2500 and 1 in 12500. The dilution which gives between 5 and 25% GFP positive cells was used to calculate the transducing units per millilitre of viral solution.

Example 3

Figure 7:
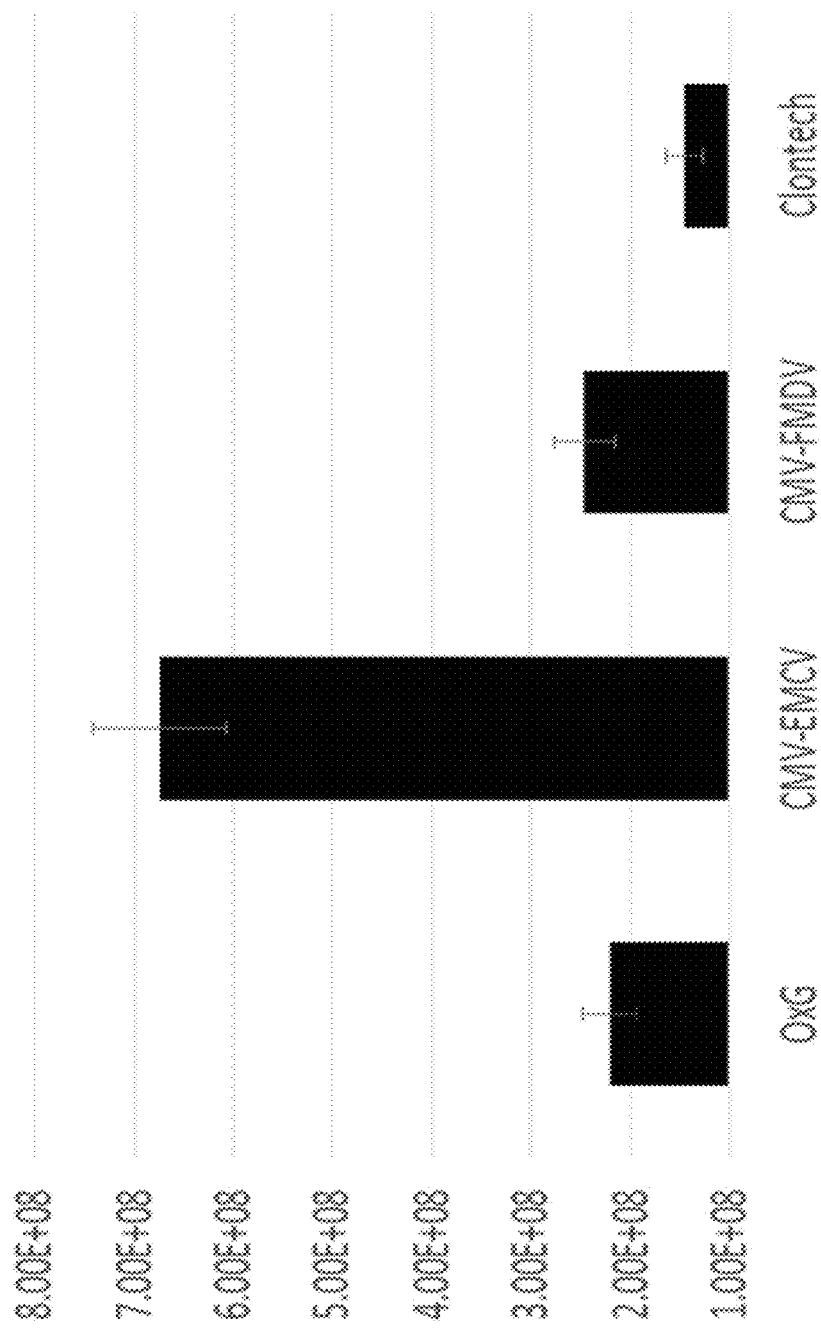
FIG. 7 shows the results of assays for the number of copies of the AAV genome per ml which were produced in cells transfected with various rep-cap plasmids. For details of the plasmids, see the above for FIGS. 3-4. Clontech refers to the 3-plasmid system supplied by Clontech (pAAV-CMV-EGFP; pHelper; pRepCap-miR342).

Plasmid vectors pSF-AAV-CMV-EGFP, pSF-Helper and one of: pSF-RepCap; pSF-CMV-Cap-EMCV-Rep78/52 or pSF-CMV-Cap-FMDV-Rep78/52 were transfected in a 1:1:1 molar ratio into 70-80% confluent HEK293T cells in a 6-well plate, to a total of 2.5 µg of DNA per well. This was run alongside the Clontech 3-plasmid system (www.clontech.com/GB/Products/Viral_Transduction/AAV_Vector_Systems/Helper_Fre e_Expression_System?sitex=10030:22372:US), also transfected as 1:1:1 molar ratio to total DNA mass 2.5 µg. Transfection reagent Lipofectamine 2000 used in a 1:2.4 ratio of total DNA mass to Lipofectamine. Entire well contents were harvested at 48 hours for analysis by qPCR. Data is presented (FIG. 7) as genome copies per mL of lysate, with error bars representing the standard error of the mean.

This experiment shows that the pSF-CMV-Cap-EMCV-Rep78/52 reliably outperforms the standard wild-type configuration used in both pSF-RepCap and the Clontech pRep-Cap-miR342. It also demonstrates that using an alternative IRES, FMDV gives an increase in viral titre, compared to the wild-type configurations.

Example 4: Enhanced Titres are Obtained without Using E2A

The effect of the presence or absence of E2A from an AAV production system of the invention was assessed using sets of plasmids which contained/did not contain the Ad5 E2A gene.

All experiments included the following plasmids:
(i) pSF-AAV-CMV-EGFP, as defined in Example 1.
(ii) pSF-CMV-Cap-EMCV-Rep. This plasmid contains the Cap sequence driven by a CMV promoter, and the Rep protein produced from the EMCV IRES.

In addition to the above (i) and (ii), the following plasmids were included in the following experiments:
a) pSF-Helper (this contains Ad5 regions E2A, E4orf6 and VA RNA I);
b) pSF-nano-CMV-E4orf6 (this contains the coding sequence for E4orf6 protein only);
c) pSF-E4orf6-VA I (this contains the full E4orf6 region and full VA RNA I sequence); and
d) OG10 (this is an empty pSF-CMV-Kan).

Figure 8:
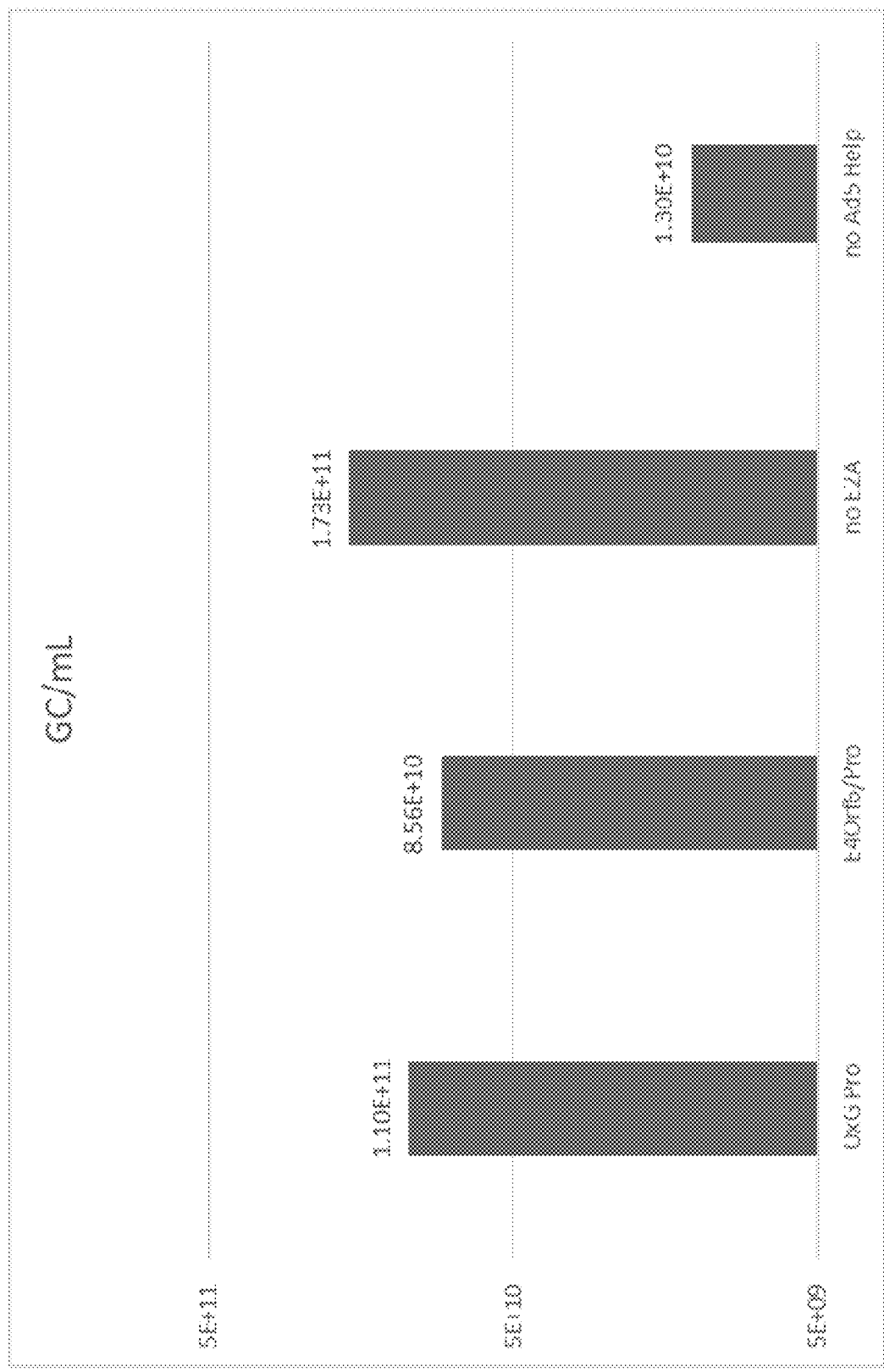
FIG. 8 shows the titres (GC, genome copies) obtained from virus produced from a) a 3-plasmid AAV system of the invention; b) the system of a) wherein pSF-helper plasmid is replaced with a plasmid containing CMV-E4orf6 (coding sequence) only; c) the system of a) wherein the pSF-helper plasmid is replaced by pSF-E4orf6-VAI; and d) the system of a) where the pSF-helper plasmid is removed and replaced with stuffer DNA (control).

The results are shown in FIG. 8, wherein the results of experiments a), b), c) and d) are shown (as genome copies/ml) labelled as "OxG Pro", "E4Orf6/Pro", "no E2A" and "no Ad5 Help", respectively.

The results show that higher titres of virus may be obtained by using a Cap/Rep plasmid of the invention without using E2A in the AAV production system.

SEQUENCES

SEQ ID NO: 1 - Rep nucleotide sequence (AAV serotype 2)
atgccggggttttacgagattgtgattaaggtccccagcgaccttgacgagcatctgcccggcatttctgacagctttgtgaa
ctgggtggccgagaaggaatgggagttgccgccagattctgacatggatctgaatctgattgagcaggcaccccctgaccg
tggccgagaagctgcagcgcgactttctgacggaatggcgccgtgtgagtaaggcccccgaggcccttttctttgtgcaatt
tgagaagggagagagctacttccacatgcacgtgctcgtggaaaccaccggggtgaaatccatgttttgggacgtttcct
gagtcagattcgcgaaaaactgattcagagaattaccgcgggatcgagccgactttgccaaactggttcgcggtcacaa
agaccagaaatggcgccggaggcgggaacaaggtggtggatgagtgctacatccccaattacttgctccccaaaaccc
agcctgagctccagtgggcgtggactaatatggaacagtattttaagcgcctgtttgaatctcacggagcgtaaacggttggt
ggcgcagcatctgacgcacgtgtcgcagacgcaggagcagaacaaagagaatcagaatcccaattctgatgcgccgg
tgatcagatcaaaaacttcagccaggtacatggagctggtcgggtggctcgtggacaaggggattacctcggagaagca
gtggatccaggaggaccaggcctcatacatctccttcaatgcggcctccaactcgcggtcccaaatcaaggctgccttgg
acaatgcgggaaagattatgagcctgactaaaaccgcccccgactacctggtgggccagcagcccgtggaggacattt
ccagcaatcggatttataaaattttggaactaaacgggtacgatcccaatatgcggcttcgtctttctgggatgggccacg
aaaaagttcggcaagaggaacaccatctggctgtttgggcctgcaactaccgggaagaccaacatcgcggaggccata
gcccacactgtgcccttctacggggtgcgtaaactggaccaatgagaactttcccttcaacgactgtgtcgacaagatggtg
atctggtgggaggagggaagatgaccgccaaggtcgtggagtcggccaaggccattctcggaggaagcaaggtgcg
cgtggaccagaaatgcaagtcctcggcccagatagacccgactcccgtgatcgtcacctccaacaccaacatgtgcgcc
gtgattgacgggaactcaacgaccttcgaacaccagcagccgttgcaagaccggatgttcaaatttgaactcacccgccg
tctggatcatgactttgggaaggtcaccaagcaggaagtcaaagacttttttccggtgggcaaaggatcacgtggttgaggt
ggagcatgaattctacgtcaaaaagggtggagccaagaaaagacccgccccagtgacgcagatataagtgagccca
aacgggtgcgcgagtcagttgcgcagccatcgacgtcagacgcggaagcttcgatcaactacgagacaggtaccaa
aacaaatgttctcgtcacgtgggcatgaatctgatgctgtttccctgcagacaatgcgagagaatgaatcagaattcaaata
tctgcttcactcacggacagaaagactgtttagagtgctttcccgtgtcagaatctcaacccgtttctgtcgtcaaaaaggcgt
atcagaaactgtgctacattcatcatatcatgggaaaggtgccagacgcttgcactgcctgcgatctggtcaatgtggatttg
gatgactgcatctttgaacaaTAG SEQ ID NO: 2 - Rep78 amino acid sequence (AAV serotype 2)
MPGFYEIVIKVPSDLDGHLPGISDSFVNWVAEKEWELPPDSDMDLNLIEQAPLTVAEKL
QRDFLTEWRRVSKAPEALFFVQFEKGESYFHMHVLVETTGVKSMVLGRFLSQIREKLI
QRIYRGIEPTLPNWFAVTKTRNGAGGGNKVVDECYIPNYLLPKTQPELQWAWTNMEQ
YLSACLNLTERKRLVAQHLTHVSQTQEQNKENQNPNSDAPVIRSKTSARYMELVGWL
VDKGITSEKQWIQEDQASYISFNAASNSRSQIKAALDNAGKIMSLTKTAPDYLVGQQPV
EDISSNRIYKILELNGYDPQYAASVFLGWATKKFGKRNTIWLFGPATTGKTNIAEAIAHT
VPFYGCVNWTNENFPFNDCVDKMVIWWEEGKMTAKVVESAKAILGGSKVRVDQKCK
SSAQIDPTPVIVTSNTNMCAVIDGNSTTFEHQQPLQDRMFKFELTRRLDHDFGKVTKQ
EVKDFFRWAKDHVVEVEHEFYVKKGGAKKRPAPSDADISEPKRVRESVAQPSTSDAE
ASINYADRYQNKCSRHVGMNLMLFPCRQCERMNQNSNICFTHGQKDCLECFPVSES
QPVSVVKKAYQKLCYIHHIMGKVPDACTACDLVNVDLDDCIFEQ*

SEQ ID NO: 3 - Rep68 amino acid sequence (AAV serotype 2)
MPGFYEIVIKVPSDLDEHLPGISDSFVNWVAEKEWELPPDSDMDLNLIEQAPLTVAEKL
QRDFLTEWRRVSKAPEALFFVQFEKGESYFHMHVLVETTGVKSMVLGRFLSQIREKLI
QRIYRGIEPTLPNWFAVTKTRNGAGGGNKVVDECYIPNYLLPKTQPELQWAWTNMEQ
YLSACLNLTERKRLVAQHLTHVSQTQEQNKENQNPNSDAPVIRSKTSARYMELVGWL
VDKGITSEKQWIQEDQASYISFNAASNSRSQIKAALDNAGKIMSLTKTAPDYLVGQQPV
EDISSNRIYKILELNGYDPQYAASVFLGWATKKFGKRNTIWLFGPATTGKTNIAEAIAHT
VPFYGCVNWTNENFPFNDCVDKMVIWWEEGKMTAKVVESAKAILGGSKVRVDQKCK
SSAQIDPTPVIVTSNTNMCAVIDGNSTTFEHQQPLQDRMFKFELTRRLDHDFGKVTKQ
EVKDFFRWAKDHVVEVEHEFYVKKGGAKKRPAPSDADISEPKRVRESVAQPSTSDAE
ASINYAD*

SEQ ID NO: 4 - Rep52 amino acid sequence (AAV serotype 2)
MELVGWLVDKGITSEKQWIQEDQASYISFNAASNSRSQIKAALDNAGKIMSLTKTAPDY
LVGQQPVEDISSNRIYKILELNGYDPQYAASVFLGWATKKFGKRNTIWLFGPATTGKTN
IAEAIAHTVPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFELTRRLDHDF
GKVTKQEVKDFFRWAKDHVVEVEHEFYVKKGGAKKRPAPSDADISEPKRVRESVAQP
STSDAEASINYADRYQNKCSRHVGMNLMLFPCRQCERMNQNSNICFTHGQKDCLECF
PVSESQPVSVVKKAYQKLCYIHHIMGKVPDACTACDLVNVDLDDCIFEQ*

SEQ ID NO: 5 - Rep40 amino acid sequence (AAV serotype 2)
MELVGWLVDKGITSEKQWIQEDQASYISFNAASNSRSQIKAALDNAGKIMSLTKTAPDY
LVGQQPVEDISSNRIYKILELNGYDPQYAASVFLGWATKKFGKRNTIWLFGPATTGKTN
IAEAIAHTVPFYGCVNWTNENFPFNDCVDKMVIWWEEGKMTAKVVESAKAILGGSKVR
VDQKCKSSAQIDPTPVIVTSNTNMCAVIDGNSTTFEHQQPLQDRMFKFELTRRLDHDF
GKVTKQEVKDFFRWAKDHVVEVEHEFYVKKGGAKKRPAPSDADISEPKRVRESVAQP
STSDAEASINYADRLARGHSL*

SEQ ID NO: 6 - Rep78 nucleotide sequence (AAV serotype 2)
atgccggggttttacgagattgtgattaaggtccccagcgaccttgacgggcatctgcccggcatttctgacagctttgtgaa
ctgggtggccgagaaggaatgggagttgccgccagattctgacatggatctgaatctgattgagcaggcaccccctgaccg
tggccgagaagctgcagcgcgactttctgacggaatggcgccgtgtgagtaaggcccccgaggcccttttctttgtgcaatt
tgagaagggagagagctacttccacatgcacgtgctcgtggaaaccaccggggtgaaatccatggtttgggacgtttcct
gagtcagattcgcgaaaaactgattcagagaattaccgcgggatcgagccgactttgccaaactggttcgcggtcacaa
agaccagaaatggcgccggaggcgggaacaaggtggtggatgagtgctacatccccaattacttgctccccaaaaccc
agcctgagctccagtgggcgtggactaatatggaacagtacctcagcgcctgtttaatctcacggagcgtaaacggttgg
tggcgcagcatctgacgcacgtgtcgcagacgcaggagcagaacaaagagaatcagaatcccaattctgatgcgccg
gtgatcagatcaaaaacttcagccaggtacatggagctggtcgggtggctcgtggacaaggggattacctcggagaagc
agtggatccaggaggaccaggcctcatacatctccttcaatgcggcctccaactcgcggtcccaaatcaaggctgccttg

| SEQUENCES |
|---|
| gacaatgcgggaaagattatgagcctgactaaaaccgcccccgactacctggtgggccagcagcccgtggaggacatt tccagcaatcggatttataaaattttggaactaaacgggtacgatccccaatatgcggcttccgtctttctgggatgggccac gaaaaagttcggcaagaggaacaccatctggctgtttgggcctgcaactaccgggaagaccaacatcgcggaggccat agcccacactgtgcccttctacggtgcgtaaactggaccaatgagaacttccttcaacgactgtgtcgacaagatggt gatctggtgggaggaggggaagatgaccgccaaggtcgtggagtcggccaaagccattctcggaggaagcaaggtgc gcgtggaccagaaatgcaagtcctcggcccagatagacccgactcccgtgatcgtcacctccaacaccaacatgtgcgc cgtgattgacgggaactcaacgaccttcgaacaccagcagccgttgcaagaccggatgttcaaattttgaactcacccgcc gtctggatcatgactttgggaaggtcaccaagcaggaagtcaaagacttttttccggtgggcaaaggatcacgtggttgagg tggagcatgaattctacgtcaaaaagggtggagccaagaaaagacccgcccccagtgacgcagatataagtgagccc aaacgggtgcgcgagtcagttgcgcagccatcgacgtcagacgcggaagcttcgatcaactacgcagacaggtacca aaacaaatgttctcgtcacgtgggcatgaatctgatgctgtttccctgcagacaatgcgagagaatgaatcagaattcaaat atctgcttcactcacggacagaaagactgtttagagtgctttcccgtgtcagaatctcaacccgtttctgtcgtcaaaaaggc gtatcagaaactgtgctacattcatcatatcatgggaaaggtgccagacgcttgcactgcctgcgatctggtcaatgtggatt tggatgactgcatctttgaacaaTAG |

SEQ ID NO: 7 - Rep68 nucleotide sequence (AAV serotype 2)
ATGCCGGGGTTTTACGAGattgtgattaaggtccccagcgaccttgacgagcatctgcccggcatttctgaca
gctttgtgaactgggtggccgagaaggaatgggagttgccgccagattctgacatggatctgaatctgattgagcaggcac
ccctgaccgtggccgagaagctgcagcgcgactttctgacgaatggcgccgtgtgagtaaggccccggaggcccttttc
tttgtgcaatttgagaagggagagagctacttccacatgcacgtgctcgtggaaccaccgggtgaaatccatggttttgg
gacgtttcctgagtcagattcgcgaaaaactgattcagaaattaccgcgggatcgagccgactttgccaaactggttcgc
ggtcacaaagaccagaaatggcgccggaggcgggaacaaggtggtggatgagtgctacatccccaattacttgctccc
caaaaccccagcctgagctccagtgggcgtGGACTAATATGGAACAGTACCTCAGCGCCTGTTTG
AATCTCACGGAgcgtaaacggttggtggccgcagcatctgacgcacgcaggagcagaacaaag
agaatcagaatcccaattctgatgcgccggtgatcagatcaaaaacttcagccaggtacatggagctggtcgggtggctc
gtggacaaggggattacctcggagaagcagtggatccaggaggaccaggcctcatacatctccttcaatgcggcctcca
actcgcggtcccaaatcaaggctgccttggacaatgcgggaaagattatgagcctgactaaaaccgcccccgactacct
ggtgggccagcagcccgtggaggacatttccagcaatcggatttataaaattttggaactaaacgggtacgatccccaat
atgcggcttccgtctttctgggatgggccacgaaaaagttcggcaagaggaacaccatctggctgtttgggcctgcaacta
ccgggaagaccaacatcgcggaggccatagcccacactgtgcccttctacggtgcgtaaactggaccaatgagaactt
tccttcaacgactgtgtcgacaagatggtgatctggtgggaggaggggaagatgaccgccaaggtcgtggagtcggcc
aaagccattctcggaggaagcaaggtgcgcgtggaccagaaatgcaagtcctcggcccagatagacccgactcccgt
gatcgtcacctccaacaccaacatgtgcgccgtgattgacgggaactcaacgaccttcgaacaccagcagccgttgcaa
gaccggatgttcaaattttgaactcacccgccgtctggatcatgactttgggaaggtcaccaagcaggaagtcaaagacttttt
tccggtgggcaaaggatcacgtggttgaggtggagcatgaattctacgtcaaaaagggtggagccaagaaaagacccg
ccccagtgacgcagatataagtgagcccaaacgggtgcgcgagtcagttgcgcagccatcgacgtcagacgcggaa
gcttcgatcaactacgcagacagTAG SEQ ID NO: 8 - Rep52 nucleotide sequence:
CATGGAGCTGGTCGGGTGGctcgtggacaaggggattacctcggagaagcagtggatccaggaggacca
ggcctcatacatctccttcaatgcggcctccaactcgcggtcccaaactcaaggctgccttggacaatgcgggaaagattat
gagcctgactaaaaccgcccccgactacctggtgggccagcagcccgtggaggacatttccagcaatcggatttataaa
attttggaactaaacgggtacgatccccaatatgcggcttccgtctttctgggatgggccacgaaaaagttcggcaagagg
aacaccatctggctgtttgggcctgcaactaccgggaagaccaacatcgcggaggccatagcccacactgtgcccttcta
cggtgcgtaaactggaccaatgagaactttccttcaacgactgtgtcgacaagatggtgatctggtgggaggagggga
agatgaccgccaaggtcgtggagtcggccaaagccattctcggaggaagcaaggtgcgcgtggaccagaaatgcaa
gtcctcggcccagatagacccgactcccgtgatcgtcacctccaacaccaacatgtgcgccgtgattgacgggaactcaa
cgaccttcgaacaccagcagccgttgcaagaccggatgttcaaattttgaactcacccgccgtctggatcatgactttggga
aggtcaccaagcaggaagtcaaagacttttttccggtgggcaaaggatcacgtggttgaggtggagcatgaattctacgtc
aaaaagggtggagccaagaaaagacccgccccagtgacgcagatataagtgagcccaaacgggtgcgcgagtca
gttgcgcagccatcgacgtcagacgcggaagcttcgatcaactacgcagacaggtaccaaaacaaatgttctcgtcacg
tgggcatgaatctgatgctgtttccctgcagacaatgcgagagaatgaatcagaattcaaatatctgcttcactcacggaca
gaaagactgtttagagtgctttcccgtgtcagaatctcaacccgtttctgtcgtcaaaaaggcgtatcagaaactgtgctacat
tcatcatatcatgggaaaggtgccagacgcttgcactgcctgcgatctggtcaatgtggatttggatgaCTGCATCTTT
GAACAATAG SEQ ID NO: 9 - Rep40 nucleotide sequence
ATGGAGCTGGTCGGGTGGctcgtggacaaggggattacctcggagaagcagtggatccaggaggaccag
gcctcatacatctccttcaatgcggcctccaactcgcggtcccaaatcaaggctgccttggacaatgcgggaaagattatg
agcctgactaaaaccgcccccgactacctggtgggccagcagcccgtggaggacatttccagcaatcggatttataaaat
tttggaactaaacgggtacgatccccaatatgcggcttccgtctttctgggatgggccacgaaaaagttcggcaagagga
acaccatctggctgtttgggcctgcaactaccgggaagaccaacatcgcggaggccatagcccacactgtgcccttctac
gggtgcgtaaactggaccaatgagaactttccttcaacgactgtgtcgacaagatggtgatctggtgggaggagggga
gatgaccgccaaggtcgtggagtcggccaaagccattctcggaggaagcaaggtgcgcgtggaccagaaatgcaagt
cctcggcccagatagacccgactcccgtgatcgtcacctccaacaccaacatgtgcgccgtgattgacgggaactcaac
gaccttcgaacaccagcagccgttgcaagaccggatgttcaaattttgaactcacccgccgtctggatcatgactttgggaa
ggtcaccaagcaggaagtcaaagacttttttccggtgggcaaaggatcacgtggttgaggtggagcatgaattctacgtca
aaaagggtggagccaagaaaagacccgccccagtgacgcagatataagtgagcccaaacgggtgcgcgagtcagt
tgcgcagccatcgacgtcagacgcggaagcttcgatcaactacgcagacagattggctcgaggacactctctcTAG SEQ ID NO: 10 - Cap nucleotide sequence (AAV serotype 2)
Cagttgcgcagccatcgacgtcagacgcggaagcttcgatcaactacgcagacaggtaccaaaacaaatgttctcgtca
cgtgggcatgaatctgatgctgtttccctgcagacaatgcgagagaatgaatcagaattcaaatatctgcttcactcacgga
cagaaagactgtttagagtgctttcccgtgtcagaatctcaacccgtttctgtcgtcaaaaaggcgtatcagaaactgtgcta
cattcatcatatcatgggaaaggtgccagacgcttgcactgcctgcgatctggtcaatgtggatttggatgactgcatctttga
acaataaatgatttaaatcaggtatggctgccgatggttatcttccagattggctcgaggacactctctctgaaggaataaga
cagtggtggaagctcaaacctggcccaccaccaccaaagcccgcagagcggcataaggacgacagcagggggtcttgt

```
gcttcctgggtacaagtacctcggacccttcaacggactcgacaagggagagccggtcaacgaggcagacgccgcgg
ccctcgagcacgacaaagcctacgaccggcagctcgacagcggagacaacccgtacctcaagtacaaccacgccga
cgcggagtttcaggagcgccttaaagaagatacgtcttttggggggcaacctcggagcagcagtcttccaggcgaaaaag
agggttcttgaacctctgggcctggttgaggaacctgttaagacggctccgggaaaaaagaggccggtagagcactctcc
tgtgggagccagactcctcctcgggaaccggaaaggcgggccagcagcctgcaagaaaaagattgaattttggtcagact
ggagacgcagactcagtacctgaccccagcctctcggacagccaccagcagccccctctggtctgggaactaatacg
atggctacaggcagtggcgcaccaatggcagacaataacgagggcgccgacggagtgggtaattcctcgggaaattg
gcattgcgattccacatggatgggcgacagagtcatcaccaccagcaccgaacctgggccctgcccacctacaacaa
ccacctctacaaacaaatttccagccaatcaggagcctcgaacgacaatcactactttggctacagcacccctgggggt
attttgacttcaacagattccactgccacttttcaccacgtgactggcaaagactcatcaacaacaactggggattccgacc
caagagactcaacttcaagtcttaacattcaagtcaaagaggtcacgcagaatgacggtacgacgacgattgccaata
accttaccagcacggttcaggtgtttactgactcggagtaccgctcccgtacgtcctcggccgtcaaggatgcct
cccgccgttcccagcagacgtcttcatggtgccacagtatggatacctcaccctgaacaacgggagtcaggcagtagga
cgctcttcattttactgcctggagtacttccttctcagatgctgcgtaccggaaacaactttaccttcagctacacttttgaggac
gttcctttccacagcagctacgctcacagccagtctgaccgtctcatgaatcctctcatcgaccagtacctgtattacttg
agcagaacaaacactccaagtggaaccaccacgcagtcaaggcttcagttttctcaggccggagcgagtgacattcgg
gaccagtctaggaactggcttcctggaccctgttaccgccagcagcgagtatcaaagacatctgcggataacaacaaca
gtgaatactcgtggactggagctaccaagtaccacctcaatggcagagactctctggtgaatccgggcccggccatggc
aagccacaaggacgatgaagaaaagtttttttcctcagagcggggttctcatctttgggaagcaaggctcagagaaaaca
aatgtggacattgaaaaggtcatgattacagacgaagaggaaatcaggacaaccaatccgtacggagcagtat
ggttctgtatctaccaacctccagagaggcaacagacaagcagctaccgcagatgtcaacacacaaggcgttcttccag
gcatggtctggcaggacagagatgtgtaccttcaggggcccatctgggcaaagattccacacacggacggacattttcac
ccctctcccctcatgggtggattcggacttaaacaccctcctccacagattctcatcaagaacaccccggtacctgcgaatc
cttcgaccaccttcagtgcggcaaagtttgcttccttcatcacacagtactccacgggacaggtcagcgtgggagatcgagtg
ggagctgcagaaggaaaacagcaaacgctggaatcccgaaattcagtacacttccaactacaacaagtctgttaatgtg
gactttactgtggacactaatggcgtgtattcagagcctcgccccattggcaccagatacctgactcgtaatctgtaA SEQ ID NO: 11 - Cap amino acid sequence (AAV serotype 2)
MAADGYLPDWLEDTLSEGIRQWWKLKPGPPPPKPAERHKDDSRGLVLPGYKYLGPF
NGLDKGEPVNEADAAALEHDKAYDRQLDSGDNPYLKYNHADAEFQERLKEDTSFGG
NLGRAVFQAKKRVLEPLGLVEEPVKTAPGKKRPVEHSPVEPDSSSGTGKAGQQPARK
RLNFGQTGDADSVPDPQPLGQPPAAPSGLGTNTMATGSGAPMADNNEGADGVGNS
SGNWHCDSTWMGDRVITTSTRTWALPTYNNHLYKQISSQSGASNDNHYFGYSTPWG
YFDFNRFHCHFSPRDWQRLINNNWGFRPKRLNFKLFNIQVKEVTQNDGTTTIANNLTS
TVQVFTDSEYQLPYVLGSAHQGCLPPFPADVFMVPQYGYLTLNNGSQAVGRSSFYCL
EYFPSQMLRTGNNFTFSYTFEDVPFHSSYAHSQSLDRLMNPLIDQYLYYLSRTNTPSG
TTTQSRLQFSQAGASDIRDQSRNWLPGPCYRQQRVSKTSADNNNSEYSWTGATKYH
LNGRDSLVNPGPAMASHKDDEEKFFPQSGVLIFGKQGSEKTNVDIEKVMITDEEEIRTT
NPVATEQYGSVSTNLQRGNRQAATADVNTQGVLPGMVWQDRDVYLQGPIWAKIPHT
DGHFHPSPLMGGFGLKHPPPQILIKNTPVPANPSTTFSAAKFASFITQYSTGQVSVEIE
WELQKENSKRWNPEIQYTSNYNKSVNVDFTVDTNGVYSEPRPIGTRYLTRNL*

SEQ ID NO: 12 - TetR binding site
tccctatcagtgatagaga

SEQ ID NO: 13- Nucleotide sequence of the TetR protein
Atgtcgcgcctggacaaaagcaaagtgattaactcagcgctggaactgttgaatgaggtgggaattgaaggactcacta
ctcgcaagctggcacagaagctgggcgtcgagcagccaacgctgtactggcatgtgaagaataaacgggcgctcctag
acgcgcttgccatcgaaatgctggaccgccatcacacccacttttgccccctggagggcgaatcctggcaagattttctgc
ggaacaatgcaaagtcgttccggtgcgctctgctgtcccaccgcgatggcgcaaaagtgcacctgggcactcggcccac
cgagaaacaatacgaaaccctggaaaaccaactggctttcctttgccaacagggattttcactggagaatgccctacg
cactatccgcggtcggccacttttaccctgggatgcgtcctcgaagatcaggagccaagtcgccaaggaggaaagag
aaactcctaccactgactcaatgcctccgctcctgagacaagccatcgagctgttcgaccaccagggtgctgaacctgcat
ttctgttcgggcttgaactgattatctgcggcctggagaaacagttgaagtgcgagtcgggatcctag SEQ ID NO: 14 - Amino acid sequence of the TetR protein
MSRLDKSKVINSALELLNEVGIEGLTTRKLAQKLGVEQPTLYWHVKNKRALLDALAIEM
LDRHHTHFCPLEGESWQDFLRNNAKSFRCALLSHRDGAKVHLGTRPTEKQYETLENQ
LAFLCQQGFSLENALYALSAVGHFTLGCVLEDQEHQVAKEERETPTTDSMPPLLRQAI
ELFDHQGAEPAFLFGLELIICGLEKQLKCESGS SEQ ID NO: 15 - EMCV IRES
CGTTACTGGCCGAAGCCGCTTGGAATAAGGCCGGTGTGCGTTTGTCTATATGTTAT
TTTCCACCATATTGCCGTCTTTTGGCAATGTGAGGGCCCGGAAACCTGGCCCTGTC
TTCTTGACGAGCATTCCTAGGGGTCTTTCCCCTCTCGCCAAAGGAATGCAAGGTCT
GTTGAATGTCGTGAAGGAAGCAGTTCCTCTGGAAGCTTCTTGAAGACAAACAACGT
CTGTAGCGACCCTTTGCAGGCAGCGGAACCCCCCACCTGGCGACAGGTGCCTCT
GCGGCCAAAAGCCACGTGTATAAGATACACCTGCAAAGGCGGCACAACCCCAGTG
CCACGTTGTGAGTTGGATAGTTGTGGAAAGAGTCAAATGGCTCCCCTCAAGCGTAT
TCAACAAGGGGCTGAAGGATGCCCAGAAGGTACCCCATTGTATGGGATCTGATCT
GGGGCCTCGGTGCACATGCTTTACATGTGTTTAGTCGAGGTTAAAAAACGTCTAGG
CCCCCCGAACCACGGGGAC SEQ ID NO: 16 - FMDV IRES
AGCAGGTTTCCCCAACTGACACAAAACGTGCAACTTGAAACTCCGCCTGGTCTTTC
CAGGTCTAGAGGGGTAACACTTTGTACTGCGTTTGGCTCCACGCTCGATCCACTG
GCGAGTGTTAGTAACAGCACTGTTGCTTCGTAGCGGAGCATGACGGCCGTGGGAA
```

| SEQUENCES |
|---|
| CTCCTCCTTGGTAACAAGGACCCACGGGGCCAAAAGCCACGCCCACACGGGCCC<br>GTCATGTGTGCAACCCCAGCACGGCGACTTTACTGCGAAACCCACTTTAAAGTGAC<br>ATTGAAACTGGTACCCACACACTGGTGACAGGCTAAGGATGCCCTTCAGGTACCC<br>CGAGGTAACACGCGACACTCGGGATCTGAGAAGGGGACTGGGGCTTCTATAAAAG<br>CGCTCGGTTTAAAAAGCTTCTATGCCTGAATAGGTGACCGGAGGTCGGCACCTTTC<br>CTTTGCAATTACTGACCAC<br><br>SEQ ID NO: 17 - Ad5 E2A<br>GGTACCCAACTCCATGCTCAACAGTCCCCAGGTACAGCCCACCCTGCGTCGCAAC<br>CAGGAACAGCTCTACAGCTTCCTGGAGCGCCACTCGCCCTACTTCCGCAGCCACA<br>GTGCGCAGATTAGGAGCGCCACTTCTTTTTGTCACTTGAAAAACATGTAAAAATAAT<br>GTACTAGAGACACTTTCAATAAAGGCAAATGCTTTTATTTGTACACTCTCGGGTGAT<br>TATTTACCCCCACCCTTGCCGTCTGCGCCGTTTAAAAATCAAAGGGGTTCTGCCGC<br>GCATCGCTATGCGCCACTGGCAGGGACACGTTGCGATACTGGTGTTTAGTGCTCC<br>ACTTAAACTCAGGCACAACCATCCGCGGCAGCTCGGTGAAGTTTTCACTCCACAG<br>GCTGCGCACCATCACCAACGCGTTTAGCAGGTCGGGCGCCGATATCTTGAAGTCG<br>CAGTTGGGGCCTCCGCCCTGCGCGCGCGAGTTGCGATACACAGGGTTGCAGCAC<br>TGGAACACTATCAGCGCCGGGTGGTGCACGCTGGCCAGCACGCTCTTGTCGGAG<br>ATCAGATCCGCGTCCAGGTCCTCCGCGTTGCTCAGGGCGAACGGAGTCAACTTTG<br>GTAGCTGCCTTCCCAAAAAGGGCGCGTGCCCAGGCTTTGAGTTGCACTCGCACCG<br>TAGTGGCATCAAAAGGTGACCGTGCCCGGTCTGGGCGTTAGGATACAGCGCCTGC<br>ATAAAAGCCTTGATCTGCTTAAAAGCCACCTGAGCCTTTGCGCCTTCAGAGAAGAA<br>CATGCCGCAAGACTTGCCGGAAAACTGATTGGCCGGACAGGCCGCGTCGTGCAC<br>GCAGCACCTTGCGTCGGTGTTGGAGATCTGCCACCACATTTCGGCCCCCACCGGTTC<br>TTCACGATCTTGGCCTTGCTAGACTGCTCCTTCAGCGCGCGCTGCCCGTTTTCGCT<br>CGTCACATCCATTTCAATCACGTGCTCCTTATTTATCATAATGCTTCCGTGTAGACA<br>CTTAAGCTCGCCTTCGATCTCAGCGCAGCGGTGCAGCCACAACGCGCAGCCCGT<br>GGGCTCGTGATGCTTGTAGGTCACCTCTGCAAACGACTGCAGGGTACGCCTGCAGG<br>AATCGCCCCATCATCGTCACAAAGGTCTTGTTGCTGGTGAAGGTCAGCTGCAACC<br>CGCGGTGCTCCTCGTTCAGCCAGGTCTTGCATACGGCCGCCAGAGCTTCCACTTG<br>GTCAGGCAGTAGTTTGAAGTTCGCCTTTAGATCGTTATCCACGTGGTACTTGTCCA<br>TCAGCGCGCGCGCAGCCTCCATGCCCTTCTCCCACGCAGACACGATCGGCACACT<br>CAGCGGGTTCATCACCGTAATTTCACTTTCCGCTTCGCTGGGCTCTTCCTCTTCCT<br>CTTGCGTCCGCATACCACGCGCCACTGGGTCGTCTTCATTCAGCCGCCGCACTGT<br>GCGCTTACCTCCTTTGCCATGCTTGATTAGCACCGGTGGGTTGCTGAAACCCACCA<br>TTTGTAGCGCCACATCTTCTCTTTCTTCCTCGCTGTCCACGATTACCTCTGGTGATG<br>GCGGGCGCTCGGGCTTGGGAGAAGGGCGCTTCTTTTTCTTCTTGGGCGCAATGGC<br>CAAATCCGCCGCCGAGGTCGATGGCCGCGGGCTGGGTGTGCGCGGCACCAGCG<br>CGTCTTGTGATGAGTCTTCCTCGTCCTCGGACTCGATACGCCGCCTCATCCGCTTT<br>TTTGGGGGCGCCCGGGGAGGCGGCGGCGACGGGGACGGGGACGACGTCCTC<br>CATGGTTGGGGGACGTCGCGCCGCACCGCGTCCGCGCTCGGGGGTGGTTTCGC<br>GCTGCTCCTCTTCCCGACTGGCCATTTCCTTCTCCTATAGGCAGAAAAAGATCATG<br>GAGTCAGTCGAGAAGAAGGACAGCCTAACCGCCCCCTCTGAGTTCGCCACCACCG<br>CCTCCACCGATGCCGCCAACGCGCTACCACCTTCCCCGTCGAGGCACCCCCGC<br>TTGAGGAGGAGGAAGTGATTATCGAGCAGGACCCAGGTTTTGTAAGCGAAGACGA<br>CGAGGACCGCTCAGTACCAACAGAGGATAAAAAGCAAGACCAGGACAACGCAGAG<br>GCAAACGAGGAACAAGTCGGGCGGGGGACGAAAGGCATGGCGACTACCTAGAT<br>GTGGGAGACGACGTGCTGTTGAAGCATCTGCAGCGCCAGTGCGCCATTATCTGCG<br>ACGCGTTGCAAGAGCGCAGCAGTGATGTGCCCCTCGCCATAGCGGATGTCAGCCTTG<br>CCTACGAACGCCACCTATTCTCACCGCGCGTACCCCCCAAACGCCAAGAAAACGG<br>CACATGCGAGCCCAACCCGCGCCTCAACTTCTACCCCGTATTTGCCGTGCCAGAG<br>GTGCTTGCCACCTATCACATCTTTTTCCAAAACTGCAAGATACCCCTATCCTGCCGT<br>GCCAACCGCAGCCGAGCGGACAAGCAGCTGGCCTTGCGGCAGGGCGCTGTCATA<br>CCTGATATCGCCTCGCTCAACGAAGTGCCAAAAATCTTTGAGGGTCTTGGACGCG<br>ACGAGAAGCGCGCGGCAAACGCTCTGCAACAGGAAAACAGCGAAAATGAAAGTCA<br>CTCTGGAGTGTTGGTGGAACTCGAGGGTGACAACGCGCGCCTAGCCGTACTAAAA<br>CGCAGCATCGAGGTCACCCACTTTGCCTACCCGGCACTTAACCTACCCCCCAAGG<br>TCATGAGCACAGTCATGAGTGAGCTGATCGTGCGCCGTGCGCAGCCCCTGGAGA<br>GGGATGCAAATTTGCAAGAACAAACAGAGGAGGGCCTACCCGCAGTTGGCGACGA<br>GCAGCTAGCGCGCTGGCTTCAAACGCGCGAGCCTGCCGACTTGGAGGAGCGACG<br>CAAACTAATGATGGCCGCAGTGCTCGTTACCGTGGAGCTTGAGTGCATGCAGCGG<br>TTCTTTGCTGACCCGGAGATGCAGCGCAAGCTAGAGGAAACATTGCACTACACCTT<br>TCGACAGGGCTACGTACGCCAGGCCTGCAAGATCTCCAACGTGGAGCTCTGCAAC<br>CTGGTCTCCTACCTTGGAATTTTGCACGAAAACCGCCTTGGGCAAAACGTGCTTCA<br>TTCCACGCTCAAGGGCGAGGCGCGCCGCGACTACGTCCGCGACTGCGTTTACTTA<br>TTTCTATGCTACACCTGGCAGACGGCCATGGGCGTTTGGCAGCAGTGCTTGGAGG<br>AGTGCAACCTCAAGGAGCTGCAGAAACTGCTAAAGCAAAACTTGAAGGACCTATG<br>GACGGCCTTCAACGAGCGCTCCGTGGCCGCGCACCTGGCGGACATCATTTTCCCC<br>GAACGCCTGCTTAAAACCCTGCAACAGGGTCTGCCAGACTTCACCAGTCAAAGCA<br>TGTTGCAGAACTTTAGGAACTTTATCCTAGAGCGCTCAGGAATCTTGCCCGCCACC<br>TGCTGTGCACTTCCTAGCGACTTTGTGCCCATTAAGTACCGCGAATGCCCTCCGCC<br>GCTTTGGGGCCACTGCTACCTTCTGCAGCTAGCCAACTACCTTGCCTACCACTCTG<br>ACATAATGGAAGACGTGAGCGGTGACGGTCTACTGGAGTGTCACTGTCGCTGCAA<br>CCTATGCACCCGCACCGCTCCCTGGTTTGCAATTCGCAGCTGCTTAACGAAAGTC<br>AAATTATCGGTACCTTTGAGCTGCAGGGTCCCTCGCCTGACGAAAAGTCCGCGGC<br>TCCGGGGTTGAAACTCACTCCGGGGCTGTGGACGTCGGCTTACCTTCGCAAATTT<br>GTACCTGAGGACTACCACGCCCACGAGATTAGGTTCTACGAAGACCAATCCCGCC |

| SEQUENCES |
|---|
| CGCCTAATGCGGAGCTTACCGCCTGCGTCATTACCCAGGGCCACATTCTTGGCCA
ATTGCAAGCCATCAACAAAGCCCGCCAAGAGTTTCTGCTACGAAAGGGACGGGGG
GTTTACTTGGACCCCCAGTCCGGCGAGGAGCTCAACCCAATCCCCCCGCCGCCG
CAGCCCTATCAGCAGCAGCCGCGGGCCCTTGCTTCCCAGGATGGCACCCAAAAA
GAAGCTGCAGCTGCCGCCGCCACCCACGGACGAGGAGGAATACTGGGACAGTCA
GGCAGAGGAGGTTTTGGACGAGGAGGAGGAGGACATGATGGAAGACTGGGAGAG
CCTAGACGAGGAAGCTTCCGAGGTCGAAGAGGTGTCAGACGAAACACCGTCACCC
TCGGTCGCATTCCCCTCGCCGGCGCCCCAGAAATCGGCAACCGGTTCCAGCATG
GCTACAACCTCCGCTCCTCAGGCGCCGCCGGCACTGCCCGTTCGCCGACCCAAC
CGTAGATGGGACACCACTGGAACCAGGGCCGGTAAGTCCAAGCAGCCGCCGCCG
TTAGCCCAAGAGCAACAACAGCGCCAAGGCTACCGCTCATGCGCGGCACAAG
AACGCCATAGTTGCTTGCTTGCAAGACTGTGGGGGCAACATCTCCTTCGCCCGCC
GCTTTCTTCTCTACCATCACGGCGTGGCCTTCCCCCGTAACATCCTGCATTACTAC
CGTCATCTCTACAGCCCATACTGCACCGGCGGCAGCGGCAGCAACAGCAGCGGC
CACACAGAAGCAAAGGCGACCGGATAGCAAGACTCTGACAAAGCCCAAGAAATCC
ACAGCGGCGGCAGCAGCAGGAGGGAGGAGCGCTGCGTCTGGCGCCCAACGAACC
CGTATCGACCCGCGAGCTTAGAAACAGGATTTTTCCCACTCTGTATGCTATATTTCA
ACAGAGCAGGGGCCAAGAACAAGAGCTGAAAATAAAAAACAGGTCTCTGCGATCC
CTCACCCGCAGCTGCCTGTATCACAAAAGCGAAGATCAGCTTCGGCGCACGCTGG
AAGACGCGGAGGCTCTCTTCAGTAAATACTGCGCGCTGACTCTTAAGGACTAGTTT
CGCGCCCTTTCTCAAATTTAAGCGCGAAAACTACGTCATCTCCAGCGGCCACACCC
GGCGCCAGCACCTGTTGTCAGCGCCATTATGAGCAAGGAAATTCCCACGCCCTAC
ATGTGGAGTTACCAGCCACAAATGGGACTTGCGGCTGGAGCTGCCCAAGACTACT
CAACCCGAATAAACTACATGAGCGCGGGACCCCACATGATATCCCGGGTCAACGG
AATACGCGCCCACCGAAACCGAATTCCCTTGGAACAGGCGGCTATTACCACCACA
CCTCGTAATAACCTTAATCCCCGTAGTTGGCCCGCTGCCCTGGTGTACCAGGAAA
GTCCCGCTCCCACCACTGTGGTACTTCCCAGAGACGCCCAGGCCGAAGTTCAGAT
GACTAACTCAGGGGCGCAGCTTGCGGGCGGCTTTCGTCACAGGGTGCGGTCGCC
CGGGC

SEQ ID NO: 18 - CMV promoter WT
AGTAATCAATTACGGGGTCATTAGTTCATAGCCCATATATGGAGTTCCGCGTTACAT
AACTTACGGTAAATGGCCCGCCTGGCTGACCGCCCAACGACCCCCGCCCATTGAC
GTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCAT
ATGCCAAGTACGCCCCCTATTGACGTCAATGACGGTAAATGGCCCGCCTGGCATT
ATGCCCAGTACATGACCTTATGGGACTTTCCTACTTGGCAGTACATCTACGTATTAG
TCATCGCTATTACCATGCTGATGCGGTTTTGGCAGTACATCAATGGGCGTGGATAG
CGGTTTGACTCACGGGGATTTCCAAGTCTCCACCCCATTGACGTCAATGGGAGTTT
GTTTTGGCACCAAAATCAACGGGACTTTCCAAAATGTCGTAACAACTCCGCCCCAT
TGACGCAAATGGGCGGTAGGCGTGTACGGTGGGAGGTCTATATAAGCAGAGCTG
GTTTAGTGAACCGTC SEQ ID NO: 19 - CMV promoter inducible (p565-2xTetO)
CGTGAGGCTCCGGTGCCCGTCAGTGGGCAGAGCGCACATCGCCCACAGTCCCG
AGAAGTTGGGGGGAGGGGTCGGCAATTGAACCGGTGCCTAGAGAAGGTGGCGCG
GGGTAAACTGGGAAAGTGATGTCGTGTACTGGCTCCGCCTTTTTCCCGAGGGTGG
GGGAGAACCGTATATAAGTGCACTAGTCGCCGTGAACGTCAATGGAAAGTCCCTA
TTGGCGTTACTATGGGAACATACGTCATTATTGACGTCAATGACGGTAAATGGCCC
GCCTGGCATTATGCCCAGTACATGACCTTATGGGACTTTCCTACTTGGCAGTACAT
CTACGTATTAGTCATCGCTATTACCATGCTGATGCGGTTTTGGCAGTACATCAATG
GGCGTGGATAGCGGTTTGACTCACGGGGATTTCCAAGTCTCCACCCCATTGACGT
CAATGGAGTTTGTTTTGGCACCAAAATCAACGGGACTTTCCAAAATGTCGTAACA
ACTCCGCCCCATTGACGCAAATGGGCGGTAGGCGTGTACGGTGGGAGGTCTATAT
AAGCAGAGCTGtccctatcagtgatagagatgtccctatcagtgatagagatcgtcgagcagctcGTTTAGTG
AACCGTCAGATC SEQ ID NO: 20 - 5' UTR sequence: Cap sequence
Cagttgcgcagccatcgacgtcagacgcggaagcttcgatcaactacgcagacaggtaccaaaacaaatgttctcgtca
cgtgggcatgaatctgatgctgtttccctgcagacaatgcgagagaatgaatcagaattcaaatatctgcttcactcacgga
cagaaagactgtttagagtgctttcccgtgtcagaatctcaacccgtttctgtcgtcaaaaaggcgtatcagaaactgtgcta
cattcatcatatcatgggaaaggtgccagacgcttgcactgcctgcgatctggtcaatgtggattttggatgactgcatctttga
acaataaatgatttaaatcaggtatggctgccgatggttatcttccagattggctcgaggacactctctctgaaggaataaga
cagtggtggaagctcaaacctggcccaccaccaccaaagcccgcagagcggcataaggacgacagcaggggtcttgt
gcttcctgggtacaagtacctcggaccccttcaacggactcgacaaggggagagccggtcaacgaggcagacgccgcgg
ccctcgagcacgacaaagcctacgaccggcagctcgacagcggagacaacccgtacctcaagtacaacacgccga
cgcggagtttcaggagcgccttaaagaagatacgtctctttgggggcaacctcggcgagcagtcttccaggcgaaaag
agggttcttgaacctctgggcctggttgaggaacctgttaagacggctccgggaaaaaagaggccggtagagcactctcc
tgtgggagccagactcctcctcgggaaccggaaaggcgggccagcagcctgcaagaaaaagattgaatttggtcagact
ggagacgcagactcagtacctgaccccagcctctcggacagccaccagcagccccctctggctctgggaactaatacg
atggctacaggcagtggcgcaccaatggcagacaataacgagggcgccgacggagtgggtaattcctcgggaaattg
gcattgcgattccacatggatgggcgacagagtcatcaccaccagcaccgaacctgggccctgcccacctacaacaa
ccacctctacaaacaaattttcagccaatcaggagcctcgaacgacaatcactactttggctacagcaccccttggggt
attttgacttcaacagattccactgccactttttcaccacgtgactggcaaagactcatcaacaacaactggggattccgacc
caagagactcaacttcaagctctttaacattcaagtcaaagaggtcacgcagaatgacggtacgacgacgattgccaata
accttaccagcacggttcaggtgtttactgactcggagtaccagctcccgtacgtcctcggctcggcgcatcaaggatgcct
cccgccgttcccagcagacgtcttcatggtgccacagtatggatacctcaccctgaacaacgggagtcaggcagtagga |

| SEQUENCES |
|---|
| cgctcttcattttactgcctggagtactttccttctcagatgctgcgtaccggaaacaactttaccttcagctacacttttgaggac<br>gttcctttccacagcagctacgctcacagccagagtctggaccgtctcatgaatcctctcatcgaccagtacctgtattacttg<br>agcagaacaaacactccaagtggaaccaccacgcagtcaaggcttcagttttctcaggccggagcgagtgacattcgg<br>gaccagtctaggaactggcttcctggaccctgttaccgccagcagcgagtatcaaagacatctgcggataacaacaaca<br>gtgaatactcgtggactggagctaccaagtaccacctcaatggcagagactctctggtgaatccgggcccggccatggc<br>aagccacaaggacgatgaagaaaagttttttcctcagagcggggttctcatctttgggaagcaaggctcagagaaaaca<br>aatgtggacattgaaaaggtcatgattacagacgaagaggaaatcaggacaaccaatcccgtggctacggagcagtat<br>ggttctgtatctaccaacctccagagaggcaacagacaagcagctaccgcagatgtcaacacacaaggcgttcttccag<br>gcatggtctggcaggacagagatgtgtaccttcaggggcccatctgggcaaagattccacacacggacggacattttcac<br>ccctctcccctcatgggtggattcggacttaaacaccctcctccacagattctcatcaagaacacccccggtacctgcgaatc<br>cttcgaccaccttcagtgcggcaaagtttgcttccttcatcacacagtactccacgggacaggtcagcgtggagatcgagtg<br>ggagctgcagaaggaaaacagcaaacgctggaatcccgaaattcagtacacttccaactacaacaagtctgttaatgtg<br>gactttactgtggacactaatggcgtgtattcagagcctcgccccattggcaccagataccgtgactcgtaatctgtaA |

SEQ ID NO: 21 - 3' UTR: Polyadenylation sequence (SV40)
CAGACATGATAAGATACATTGATGAGTTTGGACAAACCACAACTAGAATGCAGTGA
AAAAAATGCTTTATTTGTGAAATTTGTGATGCTATTGCTTTATTTGTAACCATTATAA
GCTGCAATAAACAAGTTAACAACAATTGCATTCATTTTATGTTTCAGGTTCAGG
GGGAGGTGTGGGAGGTTTTTT

The invention claimed is:

1. A nucleic acid molecule comprising:
   (i) a promoter;
   (ii) an AAV cap gene; and
   (iii) an AAV rep gene, encoding one or more Rep proteins selected from the group consisting of Rep78, Rep68, Rep52 and Rep40,
in the above 5'→3' order, wherein the cap gene and the rep gene are both operably-associated with the promoter, and wherein the rep gene is also operably-associated with an IRES (Internal Ribosome Entry Site).

2. The nucleic acid molecule as claimed in claim 1, wherein:
   (a) the rep gene encodes Rep78, Rep68, Rep52 and Rep40; or
   (b) the rep gene only encodes one, two or three of Rep78, Rep68, Rep52 and Rep40.

3. The nucleic acid molecule as claimed in claim 1, wherein the rep gene:
   (a) encodes Rep78 and Rep52, but does not encode Rep68 or Rep40;
   (b) encodes Rep68 and Rep40, but does not encode Rep78 or Rep52;
   (c) encodes Rep68 and Rep52, but does not encode Rep78 or Rep40; or
   (d) encodes Rep78 and Rep40, but does not encode Rep68 or Rep52.

4. The nucleic acid molecule as claimed in claim 2, wherein the Rep52 and/or the Rep40 are not transcribed from the promoter.

5. The nucleic acid molecule as claimed in claim 4, wherein the Rep52 and/or the Rep40 are transcribed from a p19 promoter.

6. The nucleic acid molecule as claimed in claim 1, wherein the nucleotide sequences of the rep and cap genes are from AAV serotype 2 rep or cap genes.

7. The nucleic acid molecule as claimed in claim 1, wherein the promoter is a cytomegalovirus immediate early (CMV) promoter.

8. The nucleic acid molecule as claimed in claim 1, wherein the promoter is an inducible promoter.

9. The nucleic acid molecule as claimed in claim 1, wherein the IRES is selected from the group consisting of a Picornavirus IRES, an Encephalomyocarditis virus IRES, an Aphthovirus IRES and a Foot-and-mouth disease virus IRES.

10. An RNA molecule comprising:
    (i) an AAV cap gene; and
    (ii) an AAV rep gene,
in the above 5'→3' order, wherein the rep gene is operably-associated with an IRES.

11. A plasmid or vector comprising a nucleic acid molecule as defined in claim 1.

12. A kit comprising
    (a) a plasmid or vector as claimed in claim 11, together with one or both plasmids selected from the group consisting of:
    (b) an AAV Transfer Plasmid comprising a transgene flanked by ITRs; and
    (c) a Helper Plasmid comprising one or more genes selected from the group consisting of E1A, E1B, E2A, E4 and VA.

13. A kit comprising
    (a) a plasmid or vector as defined in claim 11, together with one or both of the plasmid or cell selected from the group consisting of:
    (b) an AAV Transfer Plasmid comprising a transgene flanked by ITRs; and
    (c) a mammalian host cell comprising one or more viral genes selected from the group consisting of E1A, E1B, E2A, E4 and VA expressible from a host cell genome.

14. A mammalian cell comprising a nucleic acid molecule claim 1.

15. A process for producing an AAV packaging cell, the process comprising the steps:
    (a) stably integrating a nucleic acid molecule as claimed in claim 1 into a mammalian cell,
thereby producing a mammalian cell that expresses AAV rep and cap genes.

16. A process for producing AAVs, the process comprising the steps:
    (a) introducing a Transfer Plasmid comprising 5'- and 3'-AAV ITRs flanking a
        transgene into an AAV packaging cell, the AAV packaging cell comprising a nucleic acid molecule as claimed in claim 1 and sufficient helper genes for packaging the Transfer Plasmid, the helper genes either being present in an episomal Helper Plasmid within the cell or being integrated into the packaging cell genome;
(b) culturing the cell under conditions such that AAVs are assembled and secreted by the cell; and
(c) harvesting packaged AAVs from the supernatant, and optionally purifying the harvested AAVs.

17. The process as claimed in claim 16, wherein the helper genes do not include an E2A gene.

18. The process as claimed in claim 16, wherein the transgene encodes a protein selected from the group consisting of CRISPR enzyme, Cas9 and Cpf1, or a CRISPR sgRNA.

\* \* \* \* \*

SEQUENCE LISTING

<160> NUMBER OF SEQ ID NOS: 21

<210> SEQ ID NO 1
<211> LENGTH: 1866
<212> TYPE: DNA
<213> ORGANISM: adeno-associated virus 2

<400> SEQUENCE: 1

```
atgccggggt tttacgagat tgtgattaag gtccccagcg accttgacga gcatctgccc      60
ggcatttctg acagctttgt gaactgggtg gccgagaagg aatgggagtt gccgccagat     120
tctgacatgg atctgaatct gattgagcag gcaccctga ccgtggccga gaagctgcag      180
cgcgactttc tgacggaatg gcgccgtgtg agtaaggccc cggaggccct tttctttgtg     240
caatttgaga agggagagag ctacttccac atgcacgtgc tcgtggaaac caccggggtg     300
aaatccatgt ttttgggacg tttcctgagt cagattcgcg aaaaactgat tcagagaatt     360
taccgcggga tcgagccgac tttgccaaac tggttcgcgg tcacaaagac cagaaatggc     420 gccgaggcg ggaacaaggt ggtggatgag tgctacatcc ccaattactt gctccccaaa      480
acccagcctg agctccagtg ggcgtggact aatatggaac agtatttaag cgcctgtttg     540
aatctcacgg agcgtaaacg gttggtggcg cagcatctga cgcacgtgtc gcagacgcag     600
gagcagaaca aagagaatca gaatcccaat tctgatgcgc cggtgatcag atcaaaaact     660
tcagccaggt acatggagct ggtcgggtgg ctcgtggaca aggggattac ctcggagaag     720
cagtggatcc aggaggacca ggcctcatac atctccttca tgcggcctc caactcgcgg     780 tcccaaatca aggctgcctt ggacaatgcg ggaaagatta tgagcctgac taaaaccgcc     840
cccgactacc tggtgggcca gcagcccgtg gaggacattt ccagcaatcg gatttataaa     900
attttggaac taaacgggta cgatcccaa tatgcggctt ccgtctttct gggatgggcc      960
acgaaaaagt tcggcaagag gaacaccatc tggctgtttg ggcctgcaac taccgggaag    1020
accaacatcg cggaggccat agcccacact gtgcccttct acgggtgcgt aaactggacc    1080
aatgagaact ttcccttcaa cgactgtgtc gacaagatgg tgatctggtg ggaggagggg    1140
aagatgaccg ccaaggtcgt ggagtcggcc aaagccattc tcggaggaag caaggtcgc    1200 gtggaccaga aatgcaagtc ctcggcccag atagacccga ctcccgtgat cgtcacctcc    1260
```

```
aacaccaaca tgtgcgccgt gattgacggg aactcaacga ccttcgaaca ccagcagccg    1320
ttgcaagacc ggatgttcaa atttgaactc acccgccgtc tggatcatga ctttgggaag    1380
gtcaccaagc aggaagtcaa agacttttc cggtgggcaa aggatcacgt ggttgaggtg     1440
gagcatgaat ctacgtcaa aaagggtgga gccaagaaaa gacccgcccc cagtgacgca     1500
gatataagtg agcccaaacg ggtgcgcgag tcagttgcgc agccatcgac gtcagacgcg    1560
gaagcttcga tcaactacgc agacaggtac caaaacaaat gttctcgtca cgtgggcatg    1620
aatctgatgc tgtttccctg cagacaatgc gagagaatga atcagaattc aaatatctgc    1680
ttcactcacg gacagaaaga ctgtttagag tgctttcccg tgtcagaatc tcaacccgtt    1740
tctgtcgtca aaaaggcgta tcagaaactg tgctacattc atcatatcat gggaaaggtg    1800
ccagacgctt gcactgcctg cgatctggtc aatgtggatt tggatgactg catctttgaa    1860
caatag                                                               1866
```

<210> SEQ ID NO 2
<211> LENGTH: 621
<212> TYPE: PRT
<213> ORGANISM: adeno-associated virus 2

<400> SEQUENCE: 2

```
Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
```

```
            260                 265                 270
Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
            290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                    325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
                500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
            530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
    610                 615                 620

<210> SEQ ID NO 3
<211> LENGTH: 528
<212> TYPE: PRT
<213> ORGANISM: adeno-associated virus 2

<400> SEQUENCE: 3

Met Pro Gly Phe Tyr Glu Ile Val Ile Lys Val Pro Ser Asp Leu Asp
1               5                   10                  15
```

-continued

```
Glu His Leu Pro Gly Ile Ser Asp Ser Phe Val Asn Trp Ala Glu
            20                  25                  30
Lys Glu Trp Glu Leu Pro Pro Asp Ser Asp Met Asp Leu Asn Leu Ile
                35                  40                  45
Glu Gln Ala Pro Leu Thr Val Ala Glu Lys Leu Gln Arg Asp Phe Leu
 50                  55                  60
Thr Glu Trp Arg Arg Val Ser Lys Ala Pro Glu Ala Leu Phe Phe Val
 65                  70                  75                  80
Gln Phe Glu Lys Gly Glu Ser Tyr Phe His Met His Val Leu Val Glu
                 85                  90                  95
Thr Thr Gly Val Lys Ser Met Val Leu Gly Arg Phe Leu Ser Gln Ile
                100                 105                 110
Arg Glu Lys Leu Ile Gln Arg Ile Tyr Arg Gly Ile Glu Pro Thr Leu
                115                 120                 125
Pro Asn Trp Phe Ala Val Thr Lys Thr Arg Asn Gly Ala Gly Gly Gly
                130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
                180                 185                 190
Leu Thr His Val Ser Gln Thr Gln Glu Gln Asn Lys Glu Asn Gln Asn
                195                 200                 205
Pro Asn Ser Asp Ala Pro Val Ile Arg Ser Lys Thr Ser Ala Arg Tyr
210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
                260                 265                 270
Ile Met Ser Leu Thr Lys Thr Ala Pro Asp Tyr Leu Val Gly Gln Gln
                275                 280                 285
Pro Val Glu Asp Ile Ser Ser Asn Arg Ile Tyr Lys Ile Leu Glu Leu
290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
                340                 345                 350
Phe Tyr Gly Cys Val Asn Trp Thr Asn Glu Asn Phe Pro Phe Asn Asp
                355                 360                 365
Cys Val Asp Lys Met Val Ile Trp Trp Glu Glu Gly Lys Met Thr Ala
370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
                420                 425                 430
Thr Thr Phe Glu His Gln Gln Pro Leu Gln Asp Arg Met Phe Lys Phe
```

435                 440                 445
Glu Leu Thr Arg Arg Leu Asp His Asp Phe Gly Lys Val Thr Lys Gln
450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                    485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

<210> SEQ ID NO 4
<211> LENGTH: 397
<212> TYPE: PRT
<213> ORGANISM: adeno-associated virus 2

<400> SEQUENCE: 4

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

```
Ala Gln Pro Ser Thr Ser Asp Ala Glu Ala Ser Ile Asn Tyr Ala Asp
    290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Ala Tyr Gln Lys Leu Cys Tyr
        355                 360                 365

Ile His His Ile Met Gly Lys Val Pro Asp Ala Cys Thr Ala Cys Asp
    370                 375                 380

Leu Val Asn Val Asp Leu Asp Asp Cys Ile Phe Glu Gln
385                 390                 395

<210> SEQ ID NO 5
<211> LENGTH: 312
<212> TYPE: PRT
<213> ORGANISM: adeno-associated virus 2

<400> SEQUENCE: 5

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270
```

Pro Ser Asp Ala Asp Ile Ser Glu Pro Lys Arg Val Arg Glu Ser Val
            275                 280                 285

Ala Gln Pro Ser Thr Ser Asp Ala Glu Ala Ser Ile Asn Tyr Ala Asp
        290                 295                 300

Arg Leu Ala Arg Gly His Ser Leu
305                 310

<210> SEQ ID NO 6
<211> LENGTH: 1866
<212> TYPE: DNA
<213> ORGANISM: adeno-associated virus 2

<400> SEQUENCE: 6

| | | | | | |
|---|---|---|---|---|---|
| atgccggggt | tttacgagat | tgtgattaag | gtccccagcg | accttgacgg | gcatctgccc | 60 |
| ggcatttctg | acagctttgt | gaactgggtg | gccgagaagg | aatgggagtt | gccgccagat | 120 |
| tctgacatgg | atctgaatct | gattgagcag | gcacccctga | ccgtggccga | gaagctgcag | 180 |
| cgcgactttc | tgacggaatg | gcgccgtgtg | agtaaggccc | cggaggccct | tttctttgtg | 240 |
| caatttgaga | agggagagag | ctacttccac | atgcacgtgc | tcgtggaaac | caccggggtg | 300 |
| aaatccatgg | ttttgggacg | tttcctgagt | cagattcgcg | aaaaactgat | tcagagaatt | 360 |
| taccgcggga | tcgagccgac | tttgccaaac | tggttcgcgg | tcacaaagac | cagaaatggc | 420 |
| gccgaggcg | ggaacaaggt | ggtggatgag | tgctacatcc | ccaattactt | gctccccaaa | 480 |
| acccagcctg | agctccagtg | gcgtggact | aatatggaac | agtacctcag | cgcctgtttg | 540 |
| aatctcacgg | agcgtaaacg | gttggtggcg | cagcatctga | cgcacgtgtc | gcagacgcag | 600 |
| gagcagaaca | agagaatca | gaatcccaat | tctgatgcgc | cggtgatcag | atcaaaaact | 660 |
| tcagccaggt | acatggagct | ggtcgggtgg | ctcgtggaca | aggggattac | ctcggagaag | 720 |
| cagtggatcc | aggaggacca | ggcctcatac | atctccttca | atgcggcctc | caactcgcgg | 780 |
| tcccaaatca | aggctgcctt | ggacaatgcg | ggaaagatta | tgagcctgac | taaaaccgcc | 840 |
| cccgactacc | tggtgggcca | gcagcccgtg | gaggacattt | ccagcaatcg | gatttataaa | 900 |
| attttggaac | taaacgggta | cgatcccaa | tatgcggctt | ccgtctttct | gggatgggcc | 960 |
| acgaaaaagt | tcggcaagag | gaacaccatc | tggctgtttg | ggcctgcaac | taccgggaag | 1020 |
| accaacatcg | cggaggccat | agcccacact | gtgcccttct | acgggtgcgt | aaactggacc | 1080 |
| aatgagaact | ttccccttcaa | cgactgtgtc | gacaagatgg | tgatctggtg | ggaggagggg | 1140 |
| aagatgaccg | ccaaggtcgt | ggagtcggcc | aaagccattc | tcggaggaag | caaggtcgcg | 1200 |
| gtggaccaga | aatgcaagtc | ctcggcccag | atagacccga | ctcccgtgat | cgtcacctcc | 1260 |
| aacaccaaca | tgtgcgccgt | gattgacggg | aactcaacga | ccttcgaaca | ccagcagccg | 1320 |
| ttgcaagacc | ggatgttcaa | atttgaactc | acccgccgtc | tggatcatga | ctttgggaag | 1380 |
| gtcaccaagc | aggaagtcaa | agacttttc | cggtgggcaa | aggatcacgt | ggttgaggtg | 1440 |
| gagcatgaat | tctacgtcaa | aaagggtgga | gccaagaaaa | gacccgcccc | cagtgacgca | 1500 |
| gatataagtg | agcccaaacg | ggtgcgcgag | tcagttgcgc | agccatcgac | gtcagacgcg | 1560 |
| gaagcttcga | tcaactacgc | agacaggtac | caaaacaaat | gttctcgtca | cgtgggcatg | 1620 |
| aatctgatgc | tgtttccctg | cagacaatgc | gagagaatga | atcagaattc | aaatatctgc | 1680 |
| ttcactcacg | gacagaaaga | ctgtttagag | tgctttcccg | tgtcagaatc | tcaacccgtt | 1740 |
| tctgtcgtca | aaaggcgta | tcagaaactg | tgctacattc | atcatatcat | gggaaaggtg | 1800 |
| ccagacgctt | gcactgcctg | cgatctggtc | aatgtggatt | tggatgactg | catctttgaa | 1860 |

<210> SEQ ID NO 7
<211> LENGTH: 1589
<212> TYPE: DNA
<213> ORGANISM: adeno-associated virus 2

<400> SEQUENCE: 7

| | | | | | |
|---|---|---|---|---|---|
| atgccggggt | tttacgagat | tgtgattaag | gtccccagcg | accttgacga | gcatctgccc | 60 |
| ggcatttctg | acagctttgt | gaactgggtg | gccgagaagg | aatgggagtt | gccgccagat | 120 |
| tctgacatgg | atctgaatct | gattgagcag | gcacccctga | ccgtggccga | gaagctgcag | 180 |
| cgcgactttc | tgacggaatg | gcgccgtgtg | agtaaggccc | cggaggccct | tttctttgtg | 240 |
| caatttgaga | gggagagag | ctacttccac | atgcacgtgc | tcgtggaaac | caccggggtg | 300 |
| aaatccatgg | tttttgggacg | tttcctgagt | cagattcgcg | aaaaactgat | tcagagaatt | 360 |
| taccgcggga | tcgagccgac | tttgccaaac | tggttcgcgg | tcacaaagac | cagaaatggc | 420 |
| gccggaggcg | ggaacaaggt | ggtggatgag | tgctacatcc | ccaattactt | gctccccaaa | 480 |
| acccagcctg | agctccagtg | gcgtggact | aatatggaac | agtacctcag | cgcctgtttg | 540 |
| aatctcacgg | agcgtaaacg | gttggtggcg | cagcatctga | cgcacgtgtc | gcagacgcag | 600 |
| gagcagaaca | agagaatca | gaatcccaat | tctgatgcgc | cggtgatcag | atcaaaaact | 660 |
| tcagccaggt | acatggagct | ggtcgggtgg | ctcgtggaca | aggggattac | ctcggagaag | 720 |
| cagtggatcc | aggaggacca | ggcctcatac | atctccttca | atgcggcctc | caactcgcgg | 780 |
| tcccaaatca | aggctgcctt | ggacaatgcg | ggaaagatta | tgagcctgac | taaaaccgcc | 840 |
| cccgactacc | tggtgggcca | gcagcccgtg | gaggacattt | ccagcaatcg | gatttataaa | 900 |
| attttggaac | taaacgggta | cgatccccaa | tatgcggctt | ccgtcttcct | gggatgggcc | 960 |
| acgaaaaagt | tcggcaagag | gaacaccatc | tggctgtttg | gcctgcaac | taccgggaag | 1020 |
| accaacatcg | cggaggccat | agcccacact | gtgcccttct | acgggtgcgt | aaactggacc | 1080 |
| aatgagaact | ttcccttcaa | cgactgtgtc | gacaagatgg | tgatctggtg | ggaggagggg | 1140 |
| aagatgaccg | ccaaggtcgt | ggagtcggcc | aaagccattc | tcggaggaag | caaggtcgc | 1200 |
| gtggaccaga | aatgcaagtc | ctcggcccag | atagacccga | ctcccgtgat | cgtcacctcc | 1260 |
| aacaccaaca | tgtgcgccgt | gattgacggg | aactcaacga | ccttcgaaca | ccagcagccg | 1320 |
| ttgcaagacc | ggatgttcaa | atttgaactc | acccgccgtc | tggatcatga | ctttgggaag | 1380 |
| gtcaccaagc | aggaagtcaa | agacttttc | cggtgggcaa | aggatcacgt | ggttgaggtg | 1440 |
| gagcatgaat | tctacgtcaa | aaagggtgga | gccaagaaaa | gacccgcccc | cagtgacgca | 1500 |
| gatataagtg | agcccaaacg | ggtgcgcgag | tcagttgcgc | agccatcgac | gtcagacgcg | 1560 |
| gaagcttcga | tcaactacgc | agacagtag | | | | 1589 |

<210> SEQ ID NO 8
<211> LENGTH: 1195
<212> TYPE: DNA
<213> ORGANISM: adeno-associated virus 2

<400> SEQUENCE: 8

| | | | | | |
|---|---|---|---|---|---|
| catggagctg | gtcgggtggc | tcgtggacaa | ggggattacc | tcggagaagc | agtggatcca | 60 |
| ggaggaccag | gcctcataca | tctccttcaa | tgcggcctcc | aactcgcggt | cccaaatcaa | 120 |
| ggctgccttg | gacaatgcgg | gaaagattat | gagcctgact | aaaaccgccc | ccgactacct | 180 |

| | |
|---|---|
| ggtgggccag cagcccgtgg aggacatttc cagcaatcgg atttataaaa ttttggaact | 240 |
| aaacgggtac gatccccaat atgcggcttc cgtctttctg ggatgggcca cgaaaaagtt | 300 |
| cggcaagagg aacaccatct ggctgtttgg gcctgcaact accgggaaga ccaacatcgc | 360 |
| ggaggccata gcccacactg tgcccttcta cgggtgcgta aactggacca atgagaactt | 420 |
| tcccttcaac gactgtgtcg acaagatggt gatctggtgg aggaggggga agatgaccgc | 480 |
| caaggtcgtg gagtcggcca agccattct cggaggaagc aaggtgcgcg tggaccagaa | 540 |
| atgcaagtcc tcggcccaga tagacccgac tcccgtgatc gtcacctcca acaccaacat | 600 |
| gtgcgccgtg attacgggaa actcaacgac cttcgaacac cagcagccgt tgcaagaccg | 660 |
| gatgttcaaa tttgaactca cccgccgtct ggatcatgac tttgggaagg tcaccaagca | 720 |
| ggaagtcaaa gacttttcc ggtgggcaaa ggatcacgtg gttgaggtgg agcatgaatt | 780 |
| ctacgtcaaa aagggtggag ccaagaaaag acccgccccc agtgacgcag atataagtga | 840 |
| gcccaaacgg gtgcgcgagt cagttgcgca gccatcgacg tcagacgcgg aagcttcgat | 900 |
| caactacgca gacaggtacc aaaacaaatg ttctcgtcac gtgggcatga atctgatgct | 960 |
| gtttccctgc agacaatgcg agagaatgaa tcagaattca aatatctgct tcactcacgg | 1020 |
| acagaaagac tgtttagagt gctttcccgt gtcagaatct caacccgttt ctgtcgtcaa | 1080 |
| aaaggcgtat cagaaactgt gctacattca tcatatcatg ggaaaggtgc cagacgcttg | 1140 |
| cactgcctgc gatctggtca atgtggattt ggatgactgc atctttgaac aatag | 1195 |

<210> SEQ ID NO 9
<211> LENGTH: 939
<212> TYPE: DNA
<213> ORGANISM: adeno-associated virus 2

<400> SEQUENCE: 9

| | |
|---|---|
| atggagctgg tcgggtggct cgtggacaag gggattacct cggagaagca gtggatccag | 60 |
| gaggaccagg cctcatacat ctccttcaat gcggcctcca ctcgcggtc ccaaatcaag | 120 |
| gctgccttgg acaatgcggg aaagattatg agcctgacta aaaccgcccc cgactacctg | 180 |
| gtgggccagc agcccgtgga ggacatttcc agcaatcgga tttataaaat tttggaacta | 240 |
| aacgggtacg atccccaata tgcggcttcc gtctttctgg gatggccac gaaaaagttc | 300 |
| ggcaagagga acaccatctg gctgtttggg cctgcaacta ccgggaagac caacatcgcg | 360 |
| gaggccatag cccacactgt gcccttctac gggtgcgtaa actggaccaa tgagaacttt | 420 |
| cccttcaacg actgtgtcga caagatggtg atctggtggg aggagggga gatgaccgcc | 480 |
| aaggtcgtgg agtcggccaa agccattctc ggaggaagca aggtgcgcgt ggaccagaaa | 540 |
| tgcaagtcct cggcccagat agacccgact cccgtgatcg tcacctccaa caccaacatg | 600 |
| tgcgccgtga ttacgggaa ctcaacgacc ttcgaacacc agcagccgtt gcaagaccgg | 660 |
| atgttcaaat ttgaactcac ccgccgtctg gatcatgact ttgggaaggt caccaagcag | 720 |
| gaagtcaaag acttttccg gtgggcaaag gatcacgtg ttgaggtgga gcatgaattc | 780 |
| tacgtcaaaa agggtggagc caagaaaaga cccgccccca gtgacgcaga tataagtgag | 840 |
| cccaaacggg tgcgcgagtc agttgcgcag ccatcgacgt cagacgcgga agcttcgatc | 900 |
| aactacgcag acagattggc tcgaggacac tctctctag | 939 |

<210> SEQ ID NO 10
<211> LENGTH: 2559
<212> TYPE: DNA
<213> ORGANISM: adeno-associated virus 2

<400> SEQUENCE: 10

```
cagttgcgca gccatcgacg tcagacgcgg aagcttcgat caactacgca gacaggtacc    60
aaaacaaatg ttctcgtcac gtgggcatga atctgatgct gtttccctgc agacaatgcg   120
agagaatgaa tcagaattca aatatctgct tcactcacgg acagaaagac tgtttagagt   180
gctttcccgt gtcagaatct caacccgttt ctgtcgtcaa aaaggcgtat cagaaactgt   240
gctacattca tcatatcatg ggaaaggtgc cagacgcttg cactgcctgc gatctggtca   300
atgtggattt ggatgactgc atctttgaac aataaatgat ttaaatcagg tatggctgcc   360
gatggttatc ttccagattg gctcgaggac actctctctg aaggaataag acagtggtgg   420
aagctcaaac ctggcccacc accaccaaag cccgcagagc ggcataagga cgacagcagg   480
ggtcttgtgc ttcctgggta caagtacctc ggacccttca acggactcga caagggagag   540
ccggtcaacg aggcagacgc cgcggccctc gagcacgaca agcctacga ccggcagctc    600
gacagcggag acaacccgta cctcaagtac aaccacgccg acgcggagtt tcaggagcgc   660
cttaaagaag atacgtcttt tgggggcaac ctcggacgag cagtcttcca ggcgaaaaag   720
agggttcttg aacctctggg cctggttgag gaacctgtta agacggctcc gggaaaaaag   780
aggccggtag agcactctcc tgtggagcca gactcctcct cgggaaccgg aaaggcgggc   840
cagcagcctg caagaaaaag attgaatttt ggtcagactg gagacgcaga ctcagtacct   900
gacccccagc ctctcggaca gccaccagca gcccctctg gtctgggaac taatacgatg    960
gctacaggca gtggcgcacc aatggcagac aataacgagg cgccgacgg agtgggtaat   1020
tcctcgggaa attggcattg cgattccaca tggatgggcg acagagtcat caccaccagc  1080
acccgaacct gggccctgcc cacctacaac aaccacctct acaaacaaat tccagccaa   1140
tcaggagcct cgaacgacaa tcactacttt ggctacagca cccccttgggg gtattttgac  1200
ttcaacagat tccactgcca cttttcacca cgtgactggc aaagactcat caacaacaac  1260
tggggattcc gacccaagag actcaacttc aagctcttta acattcaagt caaagaggtc  1320
acgcagaatg acggtacgac gacgattgcc aataacctta ccagcacggt tcaggtgttt  1380
actgactcgg agtaccagct cccgtacgtc ctcggctcgg cgcatcaagg atgcctcccg  1440
ccgttcccag cagacgtctt catggtgcca cagtatggat acctcaccct gaacaacggg  1500
agtcaggcag taggacgctc ttcattttac tgcctggagt actttccttc tcagatgctg  1560
cgtaccggaa acaactttac cttcagctac acttttgagg acgttccttt ccacagcagc  1620
tacgctcaca gccagagtct ggaccgtctc atgaatcctc tcatcgacca gtacctgtat  1680
tacttgagca gaacaaacac tccaagtgga accaccacgc agtcaaggct tcagtttctc   1740
caggccgag cgagtgacat tcgggaccag tctaggaact ggcttcctgg accctgttac   1800
cgccagcagc gagtatcaaa gacatctgcg ataacaaca acagtgaata ctcgtggact   1860
ggagctacca agtaccacct caatggcaga gactctctgg tgaatccggg cccggccatg   1920
gcaagccaca aggacgatga agaaaagttt tttcctcaga gcggggttct catctttggg   1980
aagcaaggct cagagaaaac aaatgtggac attgaaaagg tcatgattac agacgaagag   2040
gaaatcagga caaccaatcc cgtggctacg agcagtatg ttctgtatc taccaacctc    2100
cagagaggca acagacaagc agctaccgca gatgtcaaca cacaaggcgt tcttccaggc   2160
atggtctggc aggacagaga tgtgtacctt caggggccca tctgggcaaa gattccacac   2220
acggacggac attttcaccc ctctccctc atgggtggat tcggacttaa acaccctcct   2280
```

-continued

```
ccacagattc tcatcaagaa cacccecggta cctgcgaatc cttcgaccac cttcagtgcg    2340
gcaaagtttg cttccttcat cacacagtac tccacgggac aggtcagcgt ggagatcgag    2400
tgggagctgc agaaggaaaa cagcaaacgc tggaatcccg aaattcagta cacttccaac    2460
tacaacaagt ctgttaatgt ggactttact gtggacacta atggcgtgta ttcagagcct    2520
cgccccattg gcaccagata cctgactcgt aatctgtaa                            2559
```

<210> SEQ ID NO 11
<211> LENGTH: 735
<212> TYPE: PRT
<213> ORGANISM: adeno-associated virus 2

<400> SEQUENCE: 11

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
```

```
              325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
            435                 440                 445
Asn Thr Pro Ser Gly Thr Thr Thr Gln Ser Arg Leu Gln Phe Ser Gln
        450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
            515                 520                 525
Asp Glu Glu Lys Phe Phe Pro Gln Ser Gly Val Leu Ile Phe Gly Lys
        530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
        610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735
```

<210> SEQ ID NO 12

<211> LENGTH: 19
<212> TYPE: DNA
<213> ORGANISM: Artificial Sequence
<220> FEATURE:
<223> OTHER INFORMATION: TetR binding site

<400> SEQUENCE: 12
tccctatcag tgatagaga                                                  19

<210> SEQ ID NO 13
<211> LENGTH: 624
<212> TYPE: DNA
<213> ORGANISM: Artificial Sequence
<220> FEATURE:
<223> OTHER INFORMATION: Nucleotide sequence of the TetR protein

<400> SEQUENCE: 13
atgtcgcgcc tggacaaaag caaagtgatt aactcagcgc tggaactgtt gaatgaggtg      60
ggaattgaag gactcactac tcgcaagctg cacagaagc tgggcgtcga gcagccaacg      120
ctgtactggc atgtgaagaa taacggcg ctcctagacg cgcttgccat cgaaatgctg       180
gaccgccatc acacccactt tgccccctg gagggcgaat cctggcaaga ttttctgcgg      240
aacaatgcaa agtcgttccg gtgcgctctg ctgtcccacc gcgatggcgc aaaagtgcac     300
ctgggcactc ggcccaccga aacaatac gaaaccctgg aaaaccaact ggctttcctt      360
tgccaacagg gattttcact ggagaatgcc ctgtacgcac tatccgcggt cggccacttt     420
accctgggat gcgtcctcga agatcaggag caccaagtcg ccaaggagga agagaaact     480 cctaccactg actcaatgcc tccgctcctg agacaagcca tcgagctgtt cgaccaccag    540
ggtgctgaac ctgcatttct gttcgggctt gaactgatta tctgcggcct ggagaaacag    600
ttgaagtgcg agtcgggatc ctag                                            624

<210> SEQ ID NO 14
<211> LENGTH: 207
<212> TYPE: PRT
<213> ORGANISM: Artificial Sequence
<220> FEATURE:
<223> OTHER INFORMATION: Amino acid sequence of the TetR protein

<400> SEQUENCE: 14

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

```
Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 15
<211> LENGTH: 519
<212> TYPE: DNA
<213> ORGANISM: Encephalomyocarditis virus

<400> SEQUENCE: 15
cgttactggc cgaagccgct tggaataagg ccggtgtgcg tttgtctata tgttattttc      60
caccatattg ccgtcttttg gcaatgtgag ggcccggaaa cctggccctg tcttcttgac     120
gagcattcct aggggtcttt cccctctcgc caaaggaatg caaggtctgt tgaatgtcgt     180
gaaggaagca gttcctctgg aagcttcttg aagacaaaca acgtctgtag cgaccctttg     240
caggcagcgg aaccccccac ctggcgacag gtgcctctgc ggccaaaagc cacgtgtata     300
agatacacct gcaaggcgg cacaacccca gtgccacgtt gtgagttgga tagttgtgga      360
aagagtcaaa tggctcccct caagcgtatt caacaagggg ctgaaggatg cccagaaggt     420
accccattgt atgggatctg atctggggcc tcggtgcaca tgctttacat gtgtttagtc     480
gaggttaaaa aacgtctagg ccccccgaac cacggggac                            519

<210> SEQ ID NO 16
<211> LENGTH: 461
<212> TYPE: DNA
<213> ORGANISM: Foot-and-mouth disease virus

<400> SEQUENCE: 16
agcaggtttc cccaactgac acaaaacgtg caacttgaaa ctccgcctgg tctttccagg      60
tctagagggg taacactttg tactgcgttt ggctccacgc tcgatccact ggcgagtgtt     120
agtaacagca ctgttgcttc gtagcggagc atgacggccg tgggaactcc tccttggtaa     180
caaggaccca cggggccaaa agccacgccc acacgggccc gtcatgtgtg caaccccagc     240
acggcgactt tactgcgaaa cccactttaa agtgacattg aaactggtac ccacacactg     300
gtgacaggct aaggatgccc ttcaggtacc ccgaggtaac acgcgacact cgggatctga     360
gaaggggact ggggcttcta taaaagcgct cggtttaaaa agcttctatg cctgaatagg     420
tgaccggagg tcggcacctt tcctttgcaa ttactgacca c                         461

<210> SEQ ID NO 17
<211> LENGTH: 5341
<212> TYPE: DNA
<213> ORGANISM: Human adenovirus type 5

<400> SEQUENCE: 17
ggtacccaac tccatgctca acagtcccca ggtacagccc accctgcgtc gcaaccagga      60
acagctctac agcttcctgg agcgccactc gccctacttc gcagccaca gtgcgcagat      120 taggagcgcc acttcttttt gtcacttgaa aaacatgtaa aaataatgta ctagagacac     180
tttcaataaa ggcaaatgct tttatttgta cactctcggg tgattattta cccccacccc     240
tgccgtctgc gccgtttaaa aatcaaaggg ttctgccgc gcatcgctat gcgccactgg     300
```

```
cagggacacg ttgcgatact ggtgtttagt gctccactta aactcaggca caaccatccg    360
cggcagctcg gtgaagtttt cactccacag gctgcgcacc atcaccaacg cgtttagcag    420
gtcgggcgcc gatatcttga agtcgcagtt ggggcctccg ccctgcgcgc gcgagttgcg    480
atacacaggg ttgcagcact ggaacactat cagcgccggg tggtgcacgc tggccagcac    540
gctcttgtcg gagatcagat ccgcgtccag gtcctccgcg ttgctcaggg cgaacggagt    600
caactttggt agctgccttc ccaaaaaggg cgcgtgccca ggctttgagt tgcactcgca    660
ccgtagtggc atcaaaaggt gaccgtgccc ggtctgggcg ttaggataca gcgcctgcat    720
aaaagccttg atctgcttaa aagccacctg agcctttgcg ccttcagaga agaacatgcc    780
gcaagacttg ccggaaaact gattggccgg acaggccgcg tcgtgcacgc agcaccttgc    840
gtcggtgttg gagatctgca ccacatttcg gccccaccgg ttcttcacga tcttggcctt    900
gctagactgc tccttcagcg cgcgctgccc gttttcgctc gtcacatcca tttcaatcac    960
gtgctcctta tttatcataa tgcttccgtg tagacactta agctcgcctt cgatctcagc   1020
gcagcggtgc agccacaacg cgcagcccgt gggctcgtga tgcttgtagg tcacctctgc   1080
aaacgactga aggtacgcct gcaggaatcg ccccatcatc gtcacaaagg tcttgttgct   1140
ggtgaaggtc agctgcaacc cgcggtgctc ctcgttcagc caggtcttgc atacggccgc   1200
cagagcttcc acttggtcag gcagtagttt gaagttcgcc tttagatcgt tatccacgtg   1260
gtacttgtcc atcagcgcgc gcgcagcctc catgcccttc tcccacgcag acacgatcgg   1320
cacactcagc gggttcatca ccgtaatttc actttccgct tcgctgggct cttcctcttc   1380
ctcttgcgtc cgcataccac gcgccactgg gtcgtcttca ttcagccgcc gcactgtgcg   1440
cttacctcct ttgccatgct tgattagcac cggtgggttg ctgaaaccca ccatttgtag   1500
cgccacatct tctctttctt cctcgctgtc cacgattacc tctggtgatg gcgggcgctc   1560
gggcttggga aagggcgct tcttttttctt cttgggcgca atggccaaat ccgccgccga   1620
ggtcgatggc cgcgggctgg gtgtgcgcgg caccagcgcg tcttgtgatg agtcttcctc   1680
gtcctcggac tcgatacgcc gcctcatccg ctttttttggg ggcgcccggg gaggcggcgg   1740
cgacggggac ggggacgaca cgtcctccat ggttgggggca cgtcgcgccg caccgcgtcc   1800
gcgctcgggg gtggtttcgc gctgctcctc ttcccgactg gccatttcct tctcctatag   1860
gcagaaaaag atcatggagt cagtcgagaa gaaggacagc ctaaccgccc cctctgagtt   1920
cgccaccacc gcctccaccg atgccgccaa cgcgcctacc accttccccg tcgaggcacc   1980
cccgcttgag gaggaggaag tgattatcga gcaggaccca ggttttgtaa gcgaagacga   2040
cgaggaccgc tcagtaccaa cagaggataa aaagcaagac caggacaacg cagaggcaaa   2100
cgaggaacaa gtcgggcggg gggacgaaag gcatggcgac tacctagatg tgggagacga   2160
cgtgctgttg aagcatctgc agcgccagtg cgccattatc tgcgacgcgt tgcaagagcg   2220
cagcgatgtg cccctcgcca tagcggatgt cagccttgcc tacgaacgcc acctattctc   2280
accgcgcgta ccccccaaac gccaagaaaa cggcacatgc gagcccaacc cgcgcctcaa   2340 cttctaccc gtatttgccg tgccagaggt gcttgccacc tatcacatct ttttccaaaa   2400
ctgcaagata cccctatcct gccgtgccaa ccgcagccga gcgacaagc agctggcctt   2460 gcggcagggc gctgtcatac ctgatatcgc ctcgctcaac gaagtgccaa aaatctttga   2520
gggtcttgga cgcgacgaga agcgcgcggc aaacgctctg caacaggaaa acagcgaaaa   2580
tgaaagtcac tctggagtgt tggtggaact cgagggtgac aacgcgcgcc tagccgtact   2640
```

```
aaaacgcagc atcgaggtca cccactttgc ctacccggca cttaacctac cccccaaggt    2700
catgagcaca gtcatgagtg agctgatcgt gcgccgtgcg cagcccctgg agagggatgc    2760
aaatttgcaa gaacaaacag aggagggcct acccgcagtt ggcgacgagc agctagcgcg    2820
ctggcttcaa acgcgcgagc ctgccgactt ggaggagcga cgcaaactaa tgatggccgc    2880
agtgctcgtt accgtggagc ttgagtgcat gcagcggttc tttgctgacc cggagatgca    2940
gcgcaagcta gaggaaacat tgcactacac ctttcgacag ggctacgtac gccaggcctg    3000
caagatctcc aacgtggagc tctgcaacct ggtctcctac cttggaattt tgcacgaaaa    3060
ccgccttggg caaaacgtgc ttcattccac gctcaagggc gaggcgcgcc gcgactacgt    3120
ccgcgactgc gtttacttat ttctatgcta cacctggcag acggccatgg gcgtttggca    3180
gcagtgcttg gaggagtgca acctcaagga gctgcagaaa ctgctaaagc aaaacttgaa    3240
ggacctatgg acggccttca acgagcgctc cgtggccgcg cacctggcgg acatcatttt    3300
ccccgaacgc ctgcttaaaa ccctgcaaca gggtctgcca gacttcacca gtcaaagcat    3360
gttgcagaac tttaggaact ttatcctaga gcgctcagga atcttgcccg ccacctgctg    3420
tgcacttcct agcgactttg tgcccattaa gtaccgcgaa tgccctccgc cgctttgggg    3480
ccactgctac cttctgcagc tagccaacta ccttgcctac cactctgaca ataatggaaga    3540 cgtgagcggt gacggtctac tggagtgtca ctgtcgctgc aacctatgca ccccgcaccg    3600
ctccctggtt tgcaattcgc agctgcttaa cgaaagtcaa attatcggta cctttgagct    3660
gcagggtccc tcgcctgacg aaaagtccgc ggctccgggg ttgaaactca ctccggggct    3720
gtggacgtcg gcttaccttc gcaaatttgt acctgaggac taccacgccc acgagattag    3780
gttctacgaa gaccaatccc gcccgcctaa tgcggagctt accgctgcg tcattaccca     3840 gggccacatt cttggccaat tgcaagccat caacaaagcc cgccaagagt ttctgctacg    3900
aaagggacgg ggggtttact tggaccccca gtccggcgag gagctcaacc caatccccccc    3960 gccgccgcag ccctatcagc agcagccgcg ggcccttgct tcccaggatg gcacccaaaa    4020
agaagctgca gctgccgccg ccacccacgg acgaggagga atactgggac agtcaggcag    4080
aggaggtttt ggacgaggag gaggaggaca tgatggaaga ctgggagagc ctagacgagg    4140
aagcttccga ggtcgaagag gtgtcagacg aaacaccgtc accctcggtc gcattcccct    4200
cgccggcgcc ccagaaatcg gcaaccggtt ccagcatggc tacaacctcc gctcctcagg    4260
cgccgccggc actgcccgtt cgccgaccca accgtagatg ggacaccact ggaaccaggg    4320
ccggtaagtc caagcagccg ccgccgttag cccaagagca caacagcgc caaggctacc     4380 gctcatggcg cgggcacaag aacgccatag ttgcttgctt gcaagactgt ggggcaaca     4440 tctccttcgc ccgccgcttt cttctctacc atcacgcgt ggccttcccc cgtaacatcc     4500
tgcattacta ccgtcatctc tacagcccat actgcaccgg cggcagcggc agcaacagca    4560
gcggccacac agaagcaaag gcgaccggat agcaagactc tgacaaagcc caagaaatcc    4620
acagcggcgg cagcagcagg aggaggagcg ctgcgtctgg cgcccaacga cccgtatcg    4680 acccgcgagc ttagaaacag gatttttccc actctgtatg ctatatttca acagagcagg    4740
ggccaagaac aagagctgaa aataaaaaac aggtctctgc gatccctcac ccgcagctgc    4800
ctgtatcaca aaagcgaaga tcagcttcgg cgcacgctgg aagacgcgga ggctctcttc    4860
agtaaatact gcgcgctgac tcttaaggac tagtttcgcg cccttttctca aatttaagcg    4920 cgaaaactac gtcatctcca gcggccacac ccggcgccag cacctgttgt cagcgccatt    4980
atgagcaagg aaattcccac gccctacatg tggagttacc agccacaaat gggacttgcg    5040
```

```
gctggagctg cccaagacta ctcaacccga ataaactaca tgagcgcggg accccacatg    5100
atatcccggg tcaacggaat acgcgcccac cgaaaccgaa ttcccttgga acaggcggct    5160
attaccacca cacctcgtaa taaccttaat ccccgtagtt ggcccgctgc cctggtgtac    5220
caggaaagtc ccgctcccac cactgtggta cttcccagag acgcccaggc cgaagttcag    5280
atgactaact caggggcgca gcttgcgggc ggctttcgtc acagggtgcg gtcgcccggg    5340
c                                                                    5341

<210> SEQ ID NO 18
<211> LENGTH: 573
<212> TYPE: DNA
<213> ORGANISM: Cytomegalovirus genus

<400> SEQUENCE: 18
agtaatcaat tacggggtca ttagttcata gcccatatat ggagttccgc gttacataac     60
ttacggtaaa tggcccgcct ggctgaccgc ccaacgaccc cgcccattg acgtcaataa    120 tgacgtatgt tcccatagta acgccaatag ggactttcca ttgacgtcaa tgggtggagt    180
atttacggta aactgcccac ttggcagtac atcaagtgta tcatatgcca agtacgcccc    240
ctattgacgt caatgacggt aaatggcccg cctggcatta tgcccagtac atgaccttat    300
gggactttcc tacttggcag tacatctacg tattagtcat cgctattacc atgctgatgc    360
ggttttggca gtacatcaat gggcgtggat agcggtttga ctcacgggga tttccaagtc    420
tccaccccat tgacgtcaat gggagtttgt tttggcacca aaatcaacgg gactttccaa    480
aatgtcgtaa caactccgcc ccattgacgc aaatgggcgg taggcgtgta cggtgggagg    540
tctatataag cagagctggt ttagtgaacc gtc                                 573

<210> SEQ ID NO 19
<211> LENGTH: 637
<212> TYPE: DNA
<213> ORGANISM: Artificial Sequence
<220> FEATURE:
<223> OTHER INFORMATION: CMV promoter inducible (p565-2xTetO)

<400> SEQUENCE: 19
cgtgaggctc cggtgcccgt cagtgggcag agcgcacatc gcccacagtc ccgagaagt     60 tgggggggagg ggtcggcaat tgaaccggtg cctagagaag gtggcgcggg gtaaactggg    120
aaagtgatgt cgtgtactgg ctccgccttt ttcccgaggg tgggggagaa ccgtatataa    180
gtgcactagt cgccgtgaac gtcaatggaa agtccctatt ggcgttacta tgggaacata    240
cgtcattatt gacgtcaatg acggtaaatg gcccgcctgg cattatgccc agtacatgac    300
cttatgggac tttcctactt ggcagtacat ctacgtatta gtcatcgcta ttaccatgct    360
gatgcggttt tggcagtaca tcaatgggcg tggatagcgg tttgactcac ggggatttcc    420
aagtctccac cccattgacg tcaatgggag tttgttttgg caccaaaatc aacgggactt    480
tccaaaatgt cgtaacaact ccgccccatt gacgcaaatg gcggtaggc gtgtacggtg    540 ggaggtctat ataagcagag ctgtccctat cagtgataga gatgtcccta tcagtgatag    600
agatcgtcga gcagctcgtt tagtgaaccg tcagatc                             637

<210> SEQ ID NO 20
<211> LENGTH: 2559
<212> TYPE: DNA
<213> ORGANISM: adeno-associated virus 2
```

```
<400> SEQUENCE: 20
cagttgcgca gccatcgacg tcagacgcgg aagcttcgat caactacgca gacaggtacc      60
aaaacaaatg ttctcgtcac gtgggcatga atctgatgct gtttccctgc agacaatgcg     120
agagaatgaa tcagaattca aatatctgct tcactcacgg acagaaagac tgtttagagt     180
gctttcccgt gtcagaatct caacccgttt ctgtcgtcaa aaaggcgtat cagaaactgt     240
gctacattca tcatatcatg ggaaaggtgc cagacgcttg cactgcctgc gatctggtca     300
atgtggattt ggatgactgc atctttgaac aataaatgat ttaaatcagg tatggctgcc     360
gatggttatc ttccagattg gctcgaggac actctctctg aaggaataag acagtggtgg     420
aagctcaaac ctggcccacc accaccaaag cccgcagagc ggcataagga cgacagcagg     480
ggtcttgtgc ttcctgggta caagtacctc ggacccttca acggactcga caagggagag     540
ccggtcaacg aggcagacgc cgcggccctc gagcacgaca agcctacga ccggcagctc      600 gacagcggag acaacccgta cctcaagtac aaccacgccg acgcggagtt tcaggagcgc     660
cttaaagaag atacgtcttt tggggcaac ctcggacgag cagtcttcca ggcgaaaaag      720
agggttcttg aacctctggg cctggttgag gaacctgtta agacggctcc gggaaaaaag     780
aggccggtag agcactctcc tgtggagcca gactcctcct cgggaaccgg aaaggcgggc     840
cagcagcctg caagaaaaag attgaatttt ggtcagactg gagacgcaga ctcagtacct     900 gaccccagc ctctcggaca gccaccagca gcccctctg gtctgggaac taatacgatg       960
gctacaggca gtggcgcacc aatggcagac aataacgagg gcgccgacgg agtgggtaat    1020
tcctcgggaa attggcattg cgattccaca tggatgggcg acagagtcat caccaccagc    1080 accgaacct gggccctgcc cacctacaac aaccacctct acaaacaaat tccagccaa      1140 tcaggagcct cgaacgacaa tcactacttt ggctacagca ccccttgggg gtattttgac    1200
ttcaacagat tccactgcca cttttcacca cgtgactggc aaagactcat caacaacaac    1260
tggggattcc gacccaagag actcaacttc aagctctttta acattcaagt caaagaggtc    1320
acgcagaatg acggtacgac gacgattgcc aataaccta ccagcacggt tcaggtgttt     1380
actgactcgg agtaccagct cccgtacgtc ctcggctcgg cgcatcaagg atgcctcccg    1440
ccgttcccag cagacgtctt catggtgcca cagtatggat acctcaccct gaacaacggg    1500
agtcaggcag taggacgctc ttcattttac tgcctggagt actttccttc tcagatgctg    1560
cgtaccggaa acaactttac cttcagctac acttttgagg acgttccttt ccacagcagc    1620
tacgctcaca gccagagtct ggaccgtctc atgaatcctc tcatcgacca gtacctgtat    1680
tacttgagca gaacaaacac tccaagtgga accaccacgc agtcaaggct tcagttttct    1740
caggccggag cgagtgacat tcgggaccag tctaggaact ggcttcctgg accctgttac    1800
cgccagcagc gagtatcaaa gacatctgcg gataacaaca cagtgaata tcgtggact     1860 ggagctacca gtaccaccct caatggcaga gactctctgg tgaatccggg cccggccatg    1920
gcaagccaca aggacgatga agaaaagttt tttcctcaga gcgggttct catctttggg     1980 aagcaaggct cagagaaaac aaatgtggac attgaaaagg tcatgattac agacgaagag    2040
gaaatcagga caaccaatcc cgtggctacg gagcagtatg ttctgtatc taccaacctc    2100 cagagaggca acagacaagc agctaccgca gatgtcaaca cacaaggcgt tcttccaggc    2160
atggtctggc aggacagaga tgtgtacctt cagggcccca tctgggcaaa gattccacac    2220
acggacggac attttcaccc ctctcccctc atgggtggat tcggacttaa acaccctcct    2280
ccacagattc tcatcaagaa cacccccgta cctgcgaatc cttcgaccac cttcagtgcg    2340
```

```
                                                   -continued gcaaagtttg cttccttcat cacacagtac tccacgggac aggtcagcgt ggagatcgag    2400
tgggagctgc agaaggaaaa cagcaaacgc tggaatcccg aaattcagta cacttccaac    2460
tacaacaagt ctgttaatgt ggactttact gtggacacta atggcgtgta ttcagagcct    2520
cgccccattg gcaccagata cctgactcgt aatctgtaa                          2559

<210> SEQ ID NO 21
<211> LENGTH: 192
<212> TYPE: DNA
<213> ORGANISM: Simian virus 40

<400> SEQUENCE: 21
cagacatgat aagatacatt gatgagtttg gacaaaccac aactagaatg cagtgaaaaa      60
aatgctttat ttgtgaaatt tgtgatgcta ttgctttatt tgtaaccatt ataagctgca     120
ataaacaagt taacaacaac aattgcattc attttatgtt tcaggttcag ggggaggtgt     180
gggaggtttt tt                                                         192
```